US009125585B2

(12) United States Patent
Rosenberg et al.

(10) Patent No.: US 9,125,585 B2
(45) Date of Patent: Sep. 8, 2015

(54) METHOD TO ENHANCE ELECTRODE LOCALIZATION OF A LEAD

(71) Applicant: PACESETTER, INC., Sylmar, CA (US)

(72) Inventors: Stuart Rosenberg, Castaic, CA (US); Thao Ngo, Shakopee, MN (US); Kyungmoo Ryu, Palmdale, CA (US); Kjell Noren, Solna (SE); Allen Keel, San Francisco, CA (US); Wenbo Hou, Santa Clarita, CA (US); Steve Koh, South Pasadena, CA (US); Michael Yang, Thousand Oaks, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 14/448,860

(22) Filed: Jul. 31, 2014

(65) Prior Publication Data

US 2014/0343652 A1   Nov. 20, 2014

Related U.S. Application Data

(62) Division of application No. 12/695,815, filed on Jan. 28, 2010, now Pat. No. 8,903,510.

(51) Int. Cl.
*A61N 1/00*        (2006.01)
*A61B 5/053*       (2006.01)
*A61N 1/05*        (2006.01)

(52) U.S. Cl.
CPC ............. *A61B 5/0538* (2013.01); *A61B 5/0536* (2013.01); *A61N 1/05* (2013.01); *A61B 2562/0209* (2013.01); *A61N 1/056* (2013.01)

(58) Field of Classification Search
CPC ..... A61N 1/0573; A61N 1/056; A61N 1/057; A61N 1/059

USPC .......................................................... 600/374
See application file for complete search history.

(56) References Cited

U.S. PATENT DOCUMENTS 4,712,555 A   12/1987   Thornander et al.
4,788,980 A   12/1988   Mann et al.
(Continued)

FOREIGN PATENT DOCUMENTS

WO   2006042039 A2    4/2006
WO   2006105394 A1   10/2006
WO   2006042039 A3    7/2007
WO   2007111542 A1   10/2007
WO   2007120290 A2   10/2007
WO   2007120290 A3    5/2008

OTHER PUBLICATIONS

Restriction Requirement, mailed May 29, 2012—U.S. Appl. No. 12/695,815.
(Continued)

*Primary Examiner* — Amanda Patton
*Assistant Examiner* — Philip Edwards

(57) ABSTRACT

An exemplary method includes positioning a lead in a patient where the lead has a longitudinal axis that extends from a proximal end to a distal end and where the lead includes an electrode with an electrical center offset from the longitudinal axis of the lead body; measuring electrical potential in a three-dimensional potential field using the electrode; and based on the measuring and the offset of the electrical center, determining lead roll about the longitudinal axis of the lead body where lead roll may be used for correction of field heterogeneity, placement or navigation of the lead or physiological monitoring (e.g., cardiac function, respiration, etc.). Various other methods, devices, systems, etc., are also disclosed.

3 Claims, 15 Drawing Sheets

(56) References Cited

U.S. PATENT DOCUMENTS

| | | | |
|---|---|---|---|
| 4,940,052 A | 7/1990 | Mann et al. | |
| 4,944,298 A | 7/1990 | Sholder | |
| 5,466,254 A | 11/1995 | Helland | |
| 5,476,483 A | 12/1995 | Bornzin et al. | |
| 6,240,307 B1 * | 5/2001 | Beatty et al. | 600/374 |
| 6,314,323 B1 | 11/2001 | Ekwall | |
| 6,807,439 B2 | 10/2004 | Edwards et al. | |
| 7,047,082 B1 | 5/2006 | Schrom et al. | |
| 7,613,500 B2 | 11/2009 | Vass et al. | |
| 7,826,881 B1 | 11/2010 | Beatty et al. | |
| 2003/0065374 A1 * | 4/2003 | Honeck | 607/127 |
| 2007/0123944 A1 | 5/2007 | Zdeblick | |
| 2007/0135721 A1 | 6/2007 | Zdeblick | |
| 2008/0058656 A1 | 3/2008 | Costello et al. | |
| 2009/0093857 A1 | 4/2009 | Markowitz et al. | |

OTHER PUBLICATIONS

NonFinal Office Action, mailed Aug. 1, 2012—U.S. Appl. No. 12/695,815.
NonFinal Office Action, mailed Dec. 17, 2012—U.S. Appl. No. 12/695,815.
Final Office Action, mailed Jul. 29, 2013—U.S. Appl. No. 12/695,815.
NonFinal Office Action, mailed Nov. 26, 2013—U.S. Appl. No. 12/695,815.
Notice of Allowance, mailed Mar. 17, 2014—U.S. Appl. No. 12/695,815.

* cited by examiner

METHOD TO ENHANCE ELECTRODE LOCALIZATION OF A LEAD

CROSS REFERENCE TO RELATED APPLICATIONS

This application is a division of U.S. patent application Ser. No. 12/695,815, filed Jan. 28, 2010.

TECHNICAL FIELD

Subject matter presented herein relates generally to localization systems and invasive therapies. Various examples pertain to lead-based electrodes that can enhance lead localization for placement, navigation or physiologic mapping. Such electrodes are optionally suited for sensing, stimulation or sensing and stimulation.

BACKGROUND

Various techniques exist to "image" internal physiology. Some of these techniques are considered "non-invasive", for example, those that rely on penetration of sound (e.g., ultrasound), electromagnetic energy (e.g., MRI, CT) or particles (e.g., PET). However, when such techniques require enhancement, clinicians often resort to intravenous delivery of contrast agents or dyes. For example, cardiac fluoroscopy can be enhanced through use of contrast agents or dyes delivered intravenously via a catheter. Further, fluoroscopy also provides some degree of visualization, which can help a clinician navigate such a catheter in a patient's body.

Another non-invasive technique is often referred to as "electrical impedance tomography" or "electrical capacitance tomography". Such techniques are referred to herein as simply "electrical tomography" (ET). Conventional ET generates images of the body related to dielectric properties and underlying physiology as reconstructed from skin-surface electrical measurements. Typically, ET involves placing electrodes on the skin and applying small alternating currents via some or all of the electrodes. In turn, corresponding electrical potentials are measured and processed to generate an image or images that represent the underlying physiology.

An invasive variation of ET is referred to herein as ET localization where one or more electrodes are introduced into the body and relied upon for physiologic mapping or localization (e.g., via delivery of electrical potentials or current, measurement of potentials or current, etc.). A particular commercially available navigation and localization system is marketed as the ENSITE® NAVX® system and technology (St. Jude Medical, Inc., Minnesota).

In a typical clinical application, the ENSITE® NAVX® system drives current across three pairs of body surface patches to create a Cartesian coordinate system in the body, in which indwelling electrodes may be located in real-time. Potentials sensed by the indwelling electrodes in the current fields can be used to compute impedances that determine a position of each electrode (e.g., in three dimensions). In various clinical applications, indwelling electrodes may be used to measure cardiac potentials and to deliver energy, for example to pace or to ablate tissue. A computed position or positions of an indwelling electrode or electrodes, in conjunction with the sensed electrograms and possibly other information, can be used to generate maps that may include anatomical features as well as information about tissue substrate and performance.

Various exemplary technologies described herein pertain to localization, navigation or both localization and navigation. Various examples are described with respect to ET. As described in below, various exemplary technologies may be optionally suited or adapted for use with imaging modalities such as MR, CT and ultrasound (e.g., ultrasound tomography, UT).

SUMMARY

An exemplary method includes positioning a lead in a patient where the lead has a longitudinal axis that extends from a proximal end to a distal end and where the lead includes an electrode with an electrical center offset from the longitudinal axis of the lead body; measuring electrical potential in a three-dimensional potential field using the electrode; and based on the measuring and the offset of the electrical center, determining lead roll about the longitudinal axis of the lead body where lead roll may be used for correction of field heterogeneity, placement or navigation of the lead or physiological monitoring (e.g., cardiac function, respiration, etc.). Various other methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Overview

As described herein, various exemplary electrodes and associated techniques can enhance localization for lead or electrode placement and navigation or physiologic mapping. For example, an exemplary electrode array and switching mechanism allows for sequential acquisition of potentials in a field generated by applied current. In such an example, the acquired potentials can be used to locate the array in a local coordinate system (e.g., including yaw, pitch and roll) or to compensate for field heterogeneities and thereby enhance location accuracy. In another example, an exemplary electrode array provides multiple, discrete electrical centers (e.g., geometric centers for electrodes of same characteristics), which may be selectable via a switching mechanism. Various other examples are described below.

Exemplary Stimulation Device

The techniques described below may be implemented in connection with a device configured or configurable to deliver cardiac therapy or to monitor cardiac condition.

Figure 1:
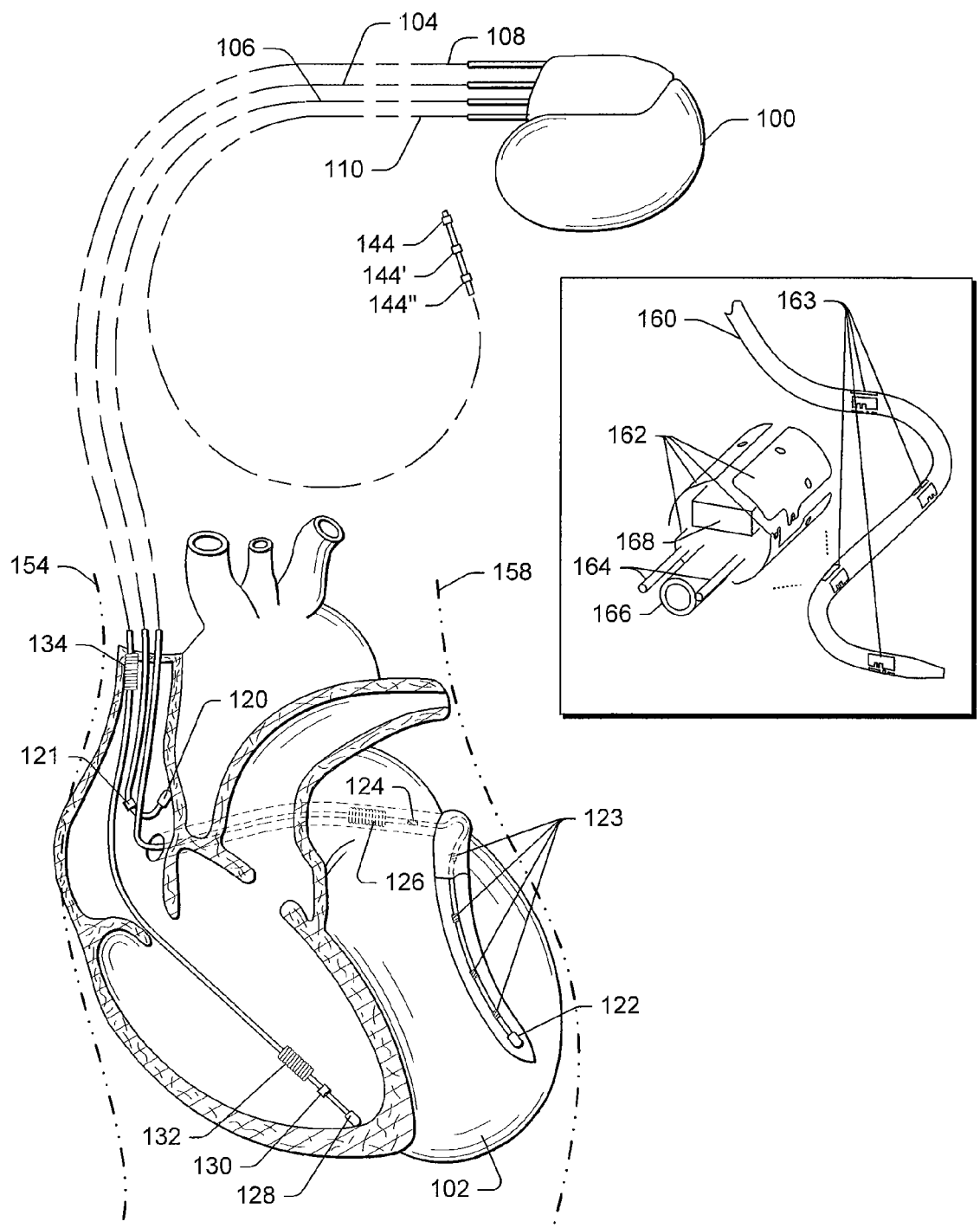
FIG. 1 is a simplified diagram illustrating an exemplary implantable stimulation device in electrical communication with at least three leads implanted into a patient's heart and at least one other lead for sensing and/or delivering stimulation and/or shock therapy. Other devices with more or fewer leads may also be suitable.

FIG. 1 shows an exemplary stimulation device 100 in electrical communication with a patient's heart 102 by way of three leads (a right atrial lead 104, a left ventricular lead 106 and a right ventricular lead 108), suitable for delivering multi-chamber stimulation and shock therapy. The leads 104, 106, 108 are optionally configurable for delivery of stimulation pulses suitable for stimulation of nerves or other tissue. In addition, in the example of FIG. 1, the device 100 includes a fourth lead 110 having multiple electrodes 144, 144', 144" suitable for stimulation of tissue and/or sensing of physiologic signals. This lead may be positioned in and/or near a patient's heart and/or remote from the heart.

FIG. 1 also shows approximate locations of the right and left phrenic nerves 154, 158. The phrenic nerve is made up mostly of motor nerve fibers for producing contractions of the diaphragm. In addition, it provides sensory innervation for various components of the mediastinum and pleura, as well as the upper abdomen (e.g., liver and gall bladder). The right phrenic nerve 154 passes over the brachiocephalic artery, posterior to the subclavian vein, and then crosses the root of the right lung anteriorly and then leaves the thorax by passing through the vena cava hiatus opening in the diaphragm at the level of T8. More specifically, with respect to the heart, the right phrenic nerve 154 passes over the right atrium while the left phrenic nerve 158 passes over the pericardium of the left ventricle and pierces the diaphragm separately. While certain therapies may call for phrenic nerve stimulation (e.g., for treatment of sleep apnea), in general, cardiac pacing therapies avoid phrenic nerve stimulation through judicious lead and electrode placement, selection of electrode configurations, adjustment of pacing parameters, etc.

Referring again to the various leads of the device 100, the right atrial lead 104, as the name implies, is positioned in and/or passes through a patient's right atrium. The right atrial lead 104 is configured to sense atrial cardiac signals and/or to provide right atrial chamber stimulation therapy. As described further below, the right atrial lead 104 may be used by the device 100 to acquire far-field ventricular signal data. As shown in FIG. 1, the right atrial lead 104 includes an atrial tip electrode 120, which typically is implanted in the patient's right atrial appendage, and an atrial ring electrode 121. The right atrial lead 104 may have electrodes other than the tip 120 and ring 121 electrodes. Further, the right atrial lead 104 may include electrodes suitable for stimulation and/or sensing located on a branch.

To sense atrial cardiac signals, ventricular cardiac signals and/or to provide chamber pacing therapy, particularly on the lett side of a patient's heart, the stimulation device 100 is coupled to the left ventricular lead 106, which in FIG. 1 is also referred to as a coronary sinus lead as it is designed for placement in the coronary sinus and/or tributary veins of the coronary sinus. As shown in FIG. 1, the coronary sinus lead 106 is configured to position at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

In the example of FIG. 1, the coronary sinus lead 106 includes a series of electrodes 123. In particular, a series of four electrodes are shown positioned in an anterior vein of the heart 102. Other coronary sinus leads may include a different number of electrodes than the lead 106. As described herein, an exemplary method selects one or more electrodes (e.g., from electrodes 123 of the lead 106) and determines characteristics associated with conduction and/or timing in the heart to aid in ventricular pacing therapy and/or assessment of cardiac condition. As described in more detail below, an illustrative method acquires information using various electrode configurations where an electrode configuration typically includes at least one electrode of a coronary sinus lead or other type of left ventricular lead. Such information may be used to determine a suitable electrode configuration for the lead 106 (e.g., selection of one or more electrodes 123 of the lead 106).

In the example of FIG. 1, as connected to the device 100, the coronary sinus lead 106 is configured for acquisition of ventricular cardiac signals (and optionally atrial signals) and to deliver left ventricular pacing therapy using, for example, at least one of the electrodes 123 and/or the tip electrode 122. The lead 106 optionally allows for left atrial pacing therapy, for example, using at least the left atrial ring electrode 124. The lead 106 optionally allows for shocking therapy, for example, using at least the left atrial coil electrode 126. For a complete description of a particular coronary sinus lead, the reader is directed to U.S. Pat. No. 5,466,254, "Coronary Sinus Lead with Atrial Sensing Capability" (Helland), which is incorporated herein by reference.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV)

coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108, as connected to the device 100, is capable of sensing or receiving cardiac signals, and delivering stimulation in the form of pacing and shock therapy to the right ventricle. An exemplary right ventricular lead may also include at least one electrode capable of stimulating other tissue; such an electrode may be positioned on the lead or a bifurcation or leg of the lead. A right ventricular lead may include a series of electrodes, such as the series 123 of the left ventricular lead 106.

FIG. 1 also shows a lead 160 as including several electrode arrays 163. In the example of FIG. 1, each electrode array 163 of the lead 160 includes a series of electrodes 162 with an associated circuit 168. Conductors 164 provide an electrical supply and return for the circuit 168. The circuit 168 includes control logic sufficient to electrically connect the conductors 164 to one or more of the electrodes of the series 162. In the example of FIG. 1, the lead 160 includes a lumen 166 suitable for receipt of a guidewire to facilitate placement of the lead 160. As described herein, any of the leads 104, 106, 108 or 110 may include one or more electrode array, optionally configured as the electrode array 163 of the lead 160. For example, the lead 106 may include features of the lead 160 and be suitable for multisite pacing for cardiac resynchronization therapy (CRT).

Figure 2:
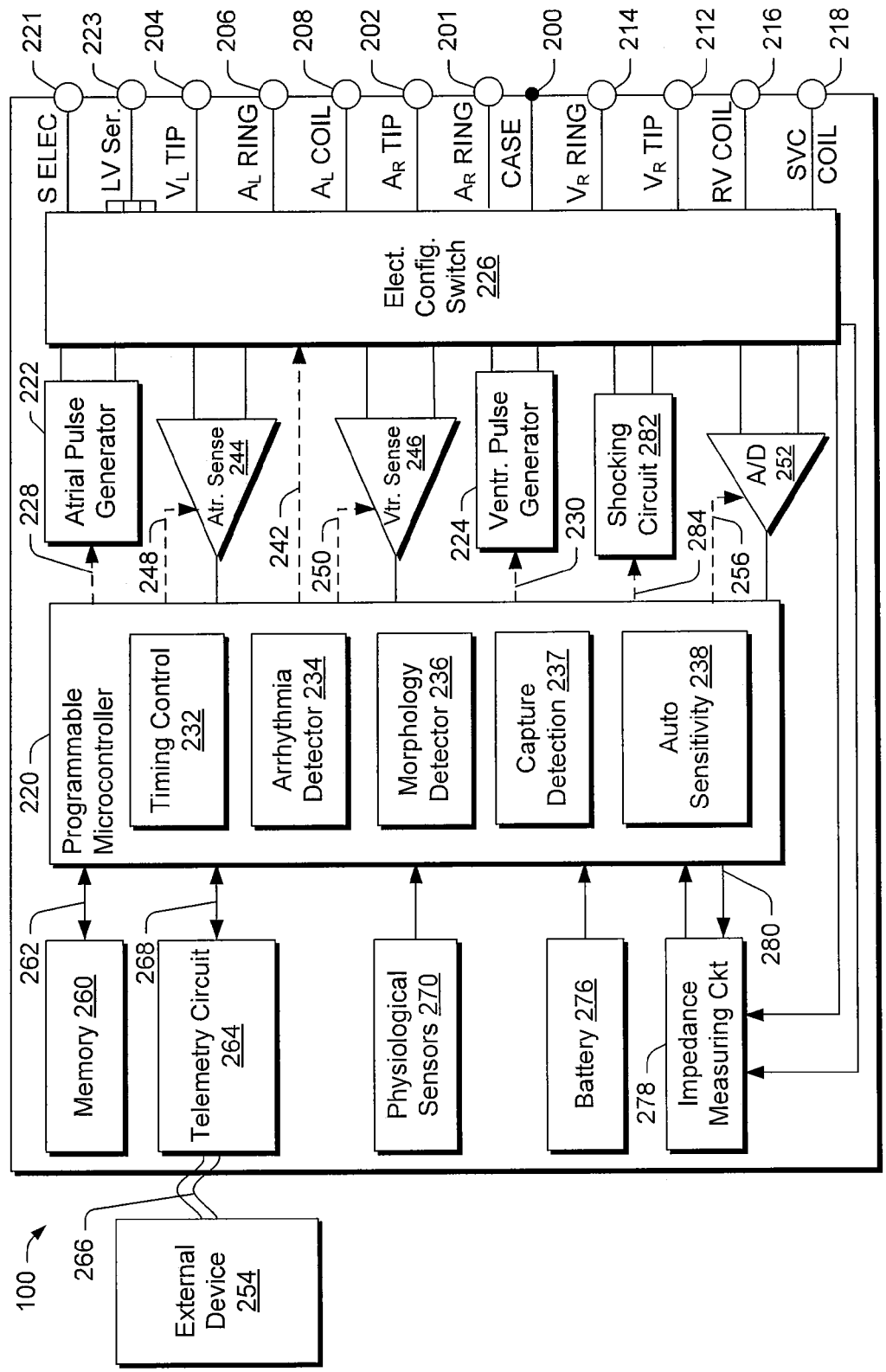
FIG. 2 is a functional block diagram of an exemplary implantable stimulation device illustrating basic elements that are configured to provide cardioversion, defibrillation, pacing stimulation and/or other tissue stimulation. The implantable stimulation device is further configured to sense information and administer therapy responsive to such information.

FIG. 2 shows an exemplary, simplified block diagram depicting various components of the device 100. The device 100 can be capable of treating both fast and slow arrhythmias with stimulation therapy, including cardioversion, defibrillation, and pacing stimulation. While a particular multi-chamber device is shown, it is to be appreciated and understood that this is for illustration purposes only. Thus, the techniques, methods, etc., described below can be implemented in connection with any suitably configured or configurable device. Accordingly, one of skill in the art could readily duplicate, eliminate, or disable the appropriate circuitry in any desired combination to provide a device capable of treating the appropriate chamber(s) or regions of a patient's heart.

Housing 200 for the device 100 is often referred to as the "can", "case" or "case electrode", and may be programmably selected to act as the return electrode for all "unipolar" modes. As described below, various exemplary techniques implement unipolar sensing for data that may include indicia of functional conduction block in myocardial tissue. Housing 200 may further be used as a return electrode alone or in combination with one or more of the coil electrodes 126, 132 and 134 for shocking or other purposes. Housing 200 further includes a connector (not shown) having a plurality of terminals 201, 202, 204, 206, 208, 212, 214, 216, 218, 221, 223 (shown schematically and, for convenience, the names of the electrodes to which they are connected are shown next to the terminals).

To achieve right atrial sensing, pacing and/or other tissue sensing, stimulation, etc., the connector includes at least a right atrial tip terminal ($A_R$ TIP) 202 adapted for connection to the right atrial tip electrode 120. A right atrial ring terminal ($A_R$ RING) 201 is also shown, which is adapted for connection to the right atrial ring electrode 121. To achieve left chamber sensing, pacing, shocking, and/or other tissue sensing, stimulation, etc., the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable stimulation electrodes is also possible via these and/or other terminals (e.g., via a stimulation terminal S ELEC 221). The terminal S ELEC 221 may optionally be used for sensing. For example, electrodes of the lead 110 may connect to the device 100 at the terminal 221 or optionally at one or more other terminals.

A terminal 223 allows for connection of a series of left ventricular electrodes. For example, the series of four electrodes 123 of the lead 106 may connect to the device 100 via the terminal 223. The terminal 223 and an electrode configuration switch 226 allow for selection of one or more of the series of electrodes and hence electrode configuration. In the example of FIG. 2, the terminal 223 includes four branches to the switch 226 where each branch corresponds to one of the four electrodes 123.

As described herein, a terminal or terminals may allow for transmission of information to a lead that includes a control circuit such as the lead 160 of FIG. 1. For example, a terminal may transmit a signal that causes the circuit 168 to select one or more of the electrodes 162 for delivery of energy to the body, for sensing electrical activity of the body or for delivery of energy and sensing activity.

To support right chamber sensing, pacing, shocking, and/or other tissue sensing, stimulation, etc., the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of cardiac or other therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that is suitable to carry out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052, the state-machine of U.S. Pat. Nos. 4,712,555 and 4,944,298, all of which are incorporated by reference herein. For a more detailed description of the various timing intervals used within the stimulation device and their inter-relationship, see U.S. Pat. No. 4,788,980, also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

The microcontroller 220 further includes timing control circuitry 232 to control the timing of the stimulation pulses (e.g., pacing rate, atrio-ventricular (AV) delay, interatrial conduction (AA) delay, or interventricular conduction (VV) delay, etc.) as well as to keep track of the timing of refractory periods, blanking intervals, noise detection windows, evoked response windows, alert intervals, marker channel timing, etc., which is well known in the art.

The microcontroller 220 further includes an arrhythmia detector 234. The detector 234 can be utilized by the stimulation device 100 for determining desirable times to administer various therapies. The detector 234 may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237 and an auto sensing module 238. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation. The capture detection module 237, as described herein, may aid in acquisition, analysis, etc., of information relating to IEGMs and, in particular, act to distinguish capture versus non-capture versus fusion.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may be selectively coupled to the right atrial lead 104, coronary sinus lead 106, and the right ventricular lead 108, through the switch 226 for detecting the presence of cardiac activity in each of the four chambers of the heart. Accordingly, the atrial and ventricular sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each of the sensing circuits 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary detector module 234, optionally uses timing intervals between sensed events (e.g., P-waves, R-waves, and depolarization signals associated with fibrillation) and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Cardiac signals are also applied to inputs of an analog-to-digital (A/D) data acquisition system 252. The data acquisition system 252 is configured to acquire intracardiac electrogram (IEGM) signals or other action potential signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or another lead (e.g., the lead 110) through the switch 226 to sample cardiac signals or other signals across any pair or other number of desired electrodes. A control signal 256 from the microcontroller 220 may instruct the A/D 252 to operate in a particular mode (e.g., resolution, amplification, etc.).

Various exemplary mechanisms for signal acquisition are described herein that optionally include use of one or more analog-to-digital converter. Various exemplary mechanisms allow for adjustment of one or more parameter associated with signal acquisition.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming and operation of the device 100.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGM) and other information (e.g., status information relating to the operation of the device 100, etc., as contained in the microcontroller 220 or memory 260) to be sent to the external device 254 through an established communication link 266.

The stimulation device 100 can further include one or more physiologic sensors 270. For example, the device 100 may include a "rate-responsive" sensor that may provide, for example, information to aid in adjustment of pacing stimulation rate according to the exercise state of the patient. However, the one or more physiological sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, VV Delay, etc.) at which the atrial and ventricular pulse generators, 222 and 224, generate stimulation pulses.

While shown as being included within the stimulation device 100, it is to be understood that one or more of the physiologic sensors 270 may also be external to the stimulation device 100, yet still be implanted within or carried by the patient. Examples of physiologic sensors that may be implemented in device 100 include known sensors that, for example, sense respiration rate, oxygen concentration of blood, pH of blood, $CO_2$ concentration of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 which is hereby incorporated by reference.

The one or more physiologic sensors 270 optionally include sensors for detecting movement and minute ventilation in the patient. Signals generated by a position sensor, a MV sensor, etc., may be passed to the microcontroller 220 for analysis in determining whether to adjust the pacing rate, etc. The microcontroller 220 may monitor the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As already mentioned, the implantable device 100 includes impedance measurement circuitry 278. Such a circuit may measure impedance or electrical resistance through use of various techniques. For example, the device 100 may deliver a low voltage (e.g., about 10 mV to about 20 mV) of alternating current between the RV tip electrode 128 and the case electrode 200. During delivery of this energy, the device 100 may measure resistance between these two electrodes where the resistance depends on any of a variety of factors. For example, the resistance may vary inversely with respect to volume of blood along the path.

In another example, resistance measurement occurs through use of a four terminal or electrode technique. For example, the exemplary device 100 may deliver an alternating current between one of the RV tip electrode 128 and the case electrode 200. During delivery, the device 100 may measure a potential between the RA ring electrode 121 and the RV ring electrode 130 where the potential is proportional to the resistance between the selected potential measurement electrodes.

With respect to two terminal or electrode techniques, where two electrodes are used to introduce current and the same two electrodes are used to measure potential, parasitic electrode-electrolyte impedances can introduce noise, especially at low current frequencies; thus, a greater number of terminals or electrodes may be used. For example, aforementioned four electrode techniques, where one electrode pair introduces current and another electrode pair measures potential, can cancel noise due to electrode-electrolyte interface impedance. Alternatively, where suitable or desirable, a two terminal or electrode technique may use larger electrode areas (e.g., even exceeding about 1 $cm^2$) and/or higher current frequencies (e.g., above about 10 kHz) to reduce noise.

Various exemplary electrodes and associated techniques can enhance localization for lead or electrode placement and navigation or physiologic mapping. With respect to the ENSITE® NAVX® localization system, heterogeneities in a current generated field can introduce errors in locating an electrode. In general, such a localization system locates the "electrical center" of an electrode, which is, in most situations, equivalent to the electrode's geometric center. Thus, as electrode size increases, an electrode will occupy a larger portion of a field and likely be exposed to more field heterogeneity. Consequently, a large electrode will be at greater risk of being inaccurately located by such a localization system. For a small electrode, a risk exists that it will be located entirely in a heterogeneous portion of a field, which can give rise to an inaccurate position determination.

Various exemplary electrodes and associated switching mechanisms or more generally acquisition mechanisms can measure or uncover field heterogeneities and thereby enhance location accuracy of a localization system. Further, various exemplary electrodes may be shaped to have geometric centers that are "asymmetric" along one or more axes (or axes of rotation). Yet further, various exemplary electrodes may be arranged as arrays where acquisition or processing of acquired information provides an indication of electrode or lead direction. Additionally, where dimensions of an electrode or an electrode array are known, the dimensions may be used to map field heterogeneities and ultimately compensate for such heterogeneities to improve accuracy of position determinations.

The ENSITE® NAVX® localization system includes a feature called "Field Scaling" that measures local variations point-by-point based on a known distance between electrodes on a lead and applies correction factors for these local variations, for example, to more accurately display anatomic features and electrode positions. Various exemplary technologies described herein can operate in conjunction with this feature to enhance performance of the localization system for position and motion of electrodes, for display of anatomy or for computation of motion-based hemodynamic surrogates.

Figure 3:
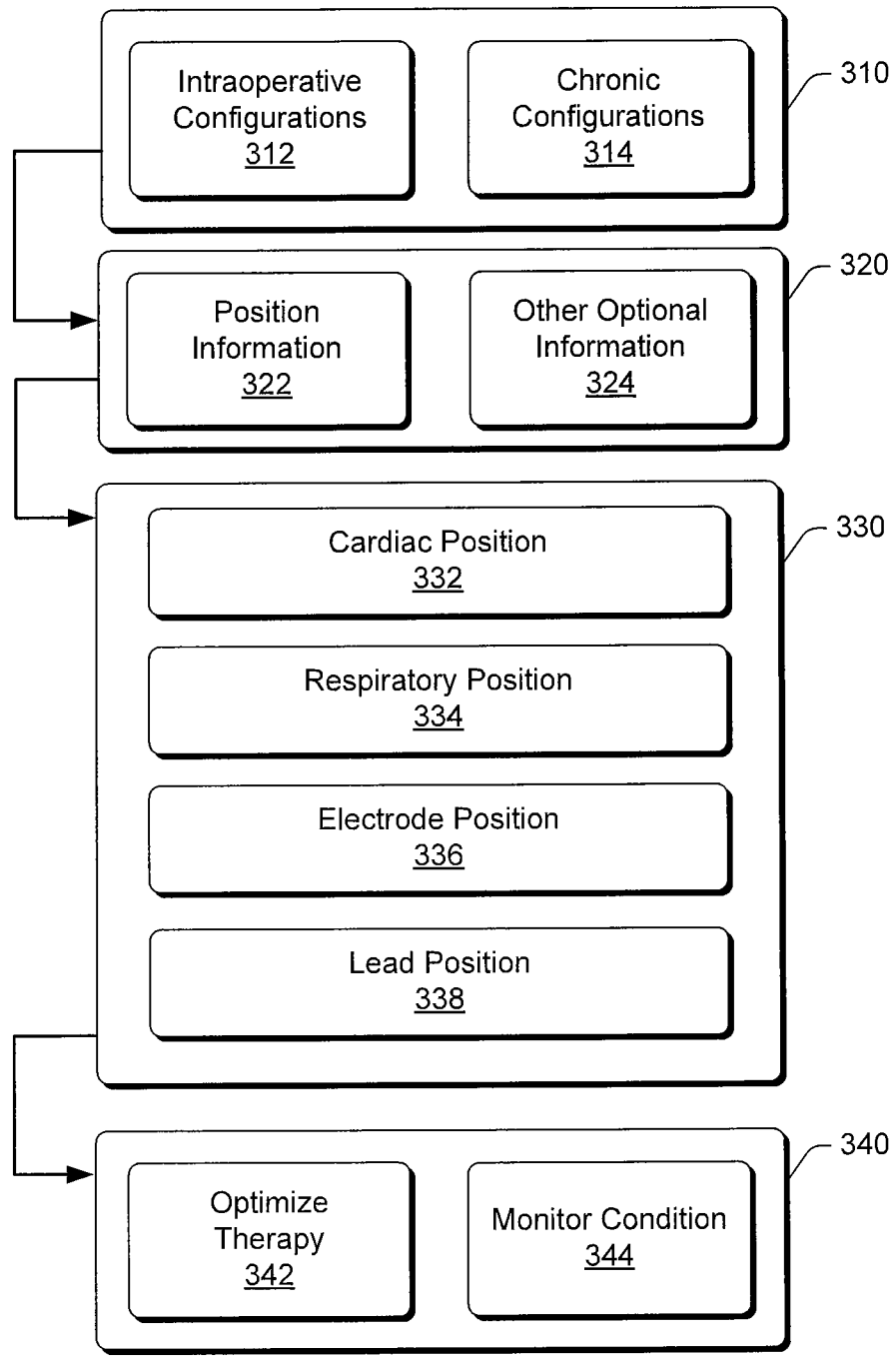
FIG. 3 is a block diagram of an exemplary method for optimizing therapy and/or monitoring conditions based at least in part on position information.

FIG. 3 shows an exemplary method 300 for acquiring and analyzing position information using a catheter or a lead with a specialized electrode or electrodes. In the description that follows, the term "lead" is used, at times, to include "catheter". In the example of FIG. 3, the method 300 includes a configurations block 310 that includes intraoperative configurations 312 (e.g., acute configurations) and chronic configurations 314. The intraoperative configurations 312 pertain to configurations that may be achieved during an operative procedure. For example, during an operative procedure, one or more leads may be positioned in a patient where the one or more leads are connected to, or variously connectable to, a device configured to acquire information and optionally to deliver electrical energy to the patient (e.g., to the heart, to a nerve, to other tissue, etc.). The chronic configurations 314 pertain to configurations achievable by a chronically implanted device and its associated lead or leads, or more generally, its electrode arrangements. In general, intraoperative configurations include those achievable by physically re-positioning a lead in a patient's body while chronic configurations normally do not allow for re-positioning as a lead or leads are usually anchored during implantation or become anchored in the weeks to months after implantation. Chronic configurations do, however, include selection of a subset of the multiple implanted electrodes, for example using a distal tip electrode versus a less distal electrode as a cathode or using the distal electrode and the less distal electrode as a bipolar pair versus using these electrodes as two independent cathodes (e.g., as independent unipolar configurations). Thus, intraoperative configurations include configurations available by changing device settings, electrode selection, and physical position of electrodes, while chronic configurations include only those configurations available by changing device settings and electrode selection, or "electronic repositioning" of one or more stimulation electrodes.

As indicated in FIG. 3, an acquisition block 320 includes acquisition of position information 322 and optionally acquisition of other information 324 (e.g., electrical information as to field homogeneity or heterogeneity, electrical activity of the heart, biosensor information, etc.). While an arrow indicates that a relationship or relationships may exist between the configurations block 310 and the acquisition block 320, acquisition of information may occur by using in part an electrode (or other equipment) that is not part of a configuration. For example, the acquisition block 320 may rely on one or more surface electrodes that define a coordinate system or location system for locating an electrode that defines one or more configurations. For example, three pairs of surface electrodes positioned on a patient may be configured to deliver current and define a three-dimensional space whereby measurement of a potential locates an electrode or electrodes in the three-dimensional space.

As described herein, an electrode may be configured for delivery of energy to the heart; for acquisition of electrical information; for acquisition of position information; for acquisition of electrical information and position information; for delivery of energy to the heart and for acquisition of electrical information; for delivery of energy to the heart and for acquisition of position information; for delivery of energy to the heart, for acquisition of electrical information and for acquisition of position information.

In various examples, acquisition of position information occurs by measuring one or more potentials where the measuring relies on an electrode or electrodes that may also be configured to deliver energy to the heart (e.g., electrical energy to pace a chamber of the heart). In such a scenario, the electrode may deliver energy sufficient to stimulate the heart and then be tracked along one or more dimensions to monitor the positional consequences of the stimulation. Further, such an electrode or electrodes may be used to acquire electrical information (e.g., an IEGM that evidences an evoked response). Such an electrode or electrodes can perform all three of these tasks with proper circuitry and control. For example, after delivery of the energy, an electrode may be configured for acquiring one or more potentials related to location and for acquiring an electrogram. To acquire potentials and an electrogram, circuitry may include gating or other sampling techniques (e.g., to avoid circuitry or interference issues). Such circuitry may rely on one sampling frequency for acquiring potentials for motion tracking and another sampling frequency for acquiring an electrogram.

The method 300 of FIG. 3 includes a determination block 330 for determining one or more of cardiac position 332, respiratory position 334 (e.g., position in the body as affected by respiration), electrode position 336 and lead position 338.

As shown in the example of FIG. 3, the conclusion block 340 may perform actions such as to optimize therapy 342 and/or to monitor patient and/or device condition 344. Information 320 or determinations 330 may be mapped or otherwise displayed with respect to anatomical features or markers. For example, as described herein, the determinations as to electrode position 336 can be used to map field heterogeneities in a multidimensional field and to compensate for such heterogeneities to improve accuracy of future position determinations. While electrical impedance tomography relies on heterogeneities to image internal physiology, various techniques described herein measure heterogeneities in a field and compensate for such heterogeneities to increase accuracy of position determinations.

As described herein, an exemplary method can include: positioning one or more electrodes within the heart and/or surrounding space (e.g., intra-chamber, intra-vascular, intra-pericardial, etc., which may be collectively referred to as "cardiac space"); and acquiring information (e.g., via one or more measured potentials) to determine a location, locations or displacement for at least one of the one or more electrodes using a localization system (e.g., the ENSITE® NAVX® system or other system with appropriate features). In such a method, the positioned electrodes may be configured for acquisition of electrical information (e.g., IEGMs). Further, with respect to acquisition of information, an acquisition system may operate at an appropriate sampling rate. For example, an acquisition system for position information may operate at a sampling rate of about 100 Hz (e.g., the ENSITE® NAVX® system can sample at about 93 Hz) and an acquisition system for electrical information may operate at a sampling rate of about 1200 Hz (e.g., in unipolar, bipolar or other polar arrangement).

Further, for an electrode array or series of electrodes, an offset or interleaving technique may be applied to acquire information from individual electrodes or groups of electrodes. A localization system or lead system may include a parallel interface, a serial interface or a parallel interface and a serial interface. Multiplexers or the like may be configured as a switch for an acquisition channel or channels. As explained with respect to the lead 160 of FIG. 1, one or more small scale circuits may be integrated into a lead (e.g., along a lead body, a lead connector or at or near an electrode array). For example, an application-specific integrated circuit (ASIC) may be provided for selectable acquisition of information from one or more electrodes or for delivery of energy by one or more electrodes. Small-scale multiplexers (MUX), including amplifiers, buffers, timers and the like, are commercially available and may be suitable for use with exemplary electrodes described herein.

An exemplary method may include preparing a patient for both implant of a device such as the device 100 of FIGS. 1 and 2 and for study using a localization system. Such preparation may occur in a relatively standard manner for implant prep, and using the ENSITE® NAVX® system or other similar technology. As described herein, any of a variety of electroanatomic mapping or localization systems that can locate indwelling electrodes in and around the heart may be used.

Once prepped, a clinician or robot may place leads and/or catheters in the patient's body, including any leads to be chronically implanted as part of a CRT system, as well as optional additional electrodes that may yield additional information (e.g., to increase accuracy by providing global information or other information).

After an initial placement of an electrode-bearing catheter or an electrode-bearing lead, a clinician may then connect one or more electrodes to an electroanatomic mapping or localization system. The term "connection" can refer to physical electrical connection or wireless connection (e.g., telemetric, RF, ultrasound, etc.) with the electrodes or wireless connection with another device that is in electrical contact with the electrodes.

Once an appropriate connection or connections have been made, real-time position data for one or more electrodes may be acquired for various configurations or conditions. For example, position data may be acquired during normal sinus rhythm; pacing in one or more chambers; advancing, withdrawing, or moving a location of an electrode; pacing one or more different electrode configurations (e.g. multisite pacing); or varying inter-stimulus timing (e.g. AV delay, VV delay).

In various examples, simultaneous to the acquisition of position information, an intracardiac electrogram (IEGM) from each electrode can also be acquired and associated with the anatomic position of the electrode. While various examples refer to simultaneous acquisition, acquisition of electrical information and acquisition of mechanical information may occur sequentially (e.g., alternate cardiac cycles) or interleaved (e.g., both acquired during the same cardiac cycle but offset by sampling time or sampling frequency).

In various exemplary methods, electrodes within the cardiac space may be optionally positioned at various locations (e.g., by continuous movement or by discrete, sequential moves), with a mapping system recording the real-time motion information at each electrode position in a point-by-point manner. Such motion data can by associated with a respective anatomic point from which it was collected. By moving the electrodes from point to point during an intervention, the motion data from each location can be incorporated into a single map, model, or parameter.

An exemplary method may include determining one or more parameters where an algorithm or a clinician may select a configuration (e.g., electrode location, multisite arrangement, AV/VV timing) that yielded the best value for one or more parameters of a CRT system and use the selected configuration as a chronic configuration for the CRT system. Such a chronic configuration may be optionally updated from time to time (e.g., during a follow-up visit, in a patient environment, etc., depending on specific capabilities of a system).

Various exemplary methods, using either a single parameter or a combination of more than one parameter, may automatically select a configuration, present an optimal configuration for acknowledgement by a clinician, or present various configurations to a clinician along with pros and cons of each configuration (e.g., in objective or subjective terms). For example, a particular configuration may be associated with a high power usage that may excessively drain a power source of an implantable device (e.g., device battery 276). Other pros and cons may pertain to patient comfort (e.g., pain, lack of pain, overall feeling, etc.).

An exemplary method may rely on certain equipment at time of implant or exploration and other equipment after implantation of a device to deliver a cardiac therapy. For example, during an intraoperative procedure, wireless communication may not be required; whereas, during a follow-up visit, measured potentials for position of chronically implanted electrodes and of measured IEGMs using chronically implanted electrodes may be communicated wirelessly from an implanted device to an external device. With respect to optimization of a chronically implanted system, in general, electrode location will not be altered, but other parameters altered to result in an optimal configuration (e.g., single- or multi-site arrangement, polarity, stimulation energy, timing parameters, etc.).

As discussed herein, various exemplary techniques deliver current and measure potential where potential varies typically with respect to cardiac mechanics (e.g., due to motion). For example, electrodes for delivery of current may be placed at locations that do not vary significantly with respect to cardiac mechanics while one or more electrodes for measuring potential may be placed at a location or locations that vary with respect to cardiac mechanics. Alternatively, electrodes for measuring potential may be placed at locations that do not vary significantly with respect to cardiac mechanics while one or more electrodes for delivery of current may be placed at a location or locations that vary with respect to cardiac mechanics. Various combinations of the foregoing arrangements are possible as well. Electrodes may be associated with a catheter or a lead. In some instances, an electrode may be a "stand-alone" electrode, such as a case electrode of an implantable device (see, e.g., the case electrode 200 of the device 100 of FIGS. 1 and 2).

In accordance with the method 300 of FIG. 3, an exemplary method may include preparing a patient for both implant and a localization study. In this example, preparation can be accomplished in standard manner for implant preparation and the mapping may rely on a localization system such as the ENSITE® NAVX® system or other similar technology for the mapping prep. After preparing the patient, the method includes placing leads and/or catheters in the patient's body, including any leads to be chronically implanted as part of a therapeutic system. After placement, the method includes connecting electrodes on leads and/or catheters to the localization system (e.g., an electroanatomic mapping system). With respect to the term "connecting", depending on the equipment, it may include physical electrical connecting and/or telemetric/RF/wireless/ultrasound/other communication connecting (e.g., directly or indirectly, via another "bridging" device, with the electrodes.)

After appropriate connections are made, acquiring or recording follows to record real-time positions of one or more electrodes for various configurations or conditions such as, but not limited to: normal sinus rhythm; pacing in one or more chambers (e.g., RV pacing, LV pacing BiV pacing); at various lead placement locations, (i.e., advancing, withdrawing, or moving the location of an electrode); pacing one or more different electrode configurations (e.g. multisite pacing); or varying inter-stimulus timing (e.g. AV delay, VV delay). After or during acquisition, the method can determine positions for one or more electrodes. Subsequently, based on the positions, optionally in conjunction with other information (e.g., other ENSITE® real-time cardiac performance parameters), a clinician or a device may select a configuration (e.g., electrode location, multisite configuration, AV/VV delays, etc.) that yielded or yields the best value(s) for a mechanical dyssynchrony parameter(s). This configuration may then be used chronically (e.g., as the final configuration of a CRT setup).

Such a method may separately be implemented at a clinic or hospital follow-up after the time of implant, provided wireless communication with the chronic indwelling electrodes. In general, it can be assumed that the electrode location will not be altered, but optimization of single- or multi-site configuration as well as timing parameter may still be performed.

Figure 4:
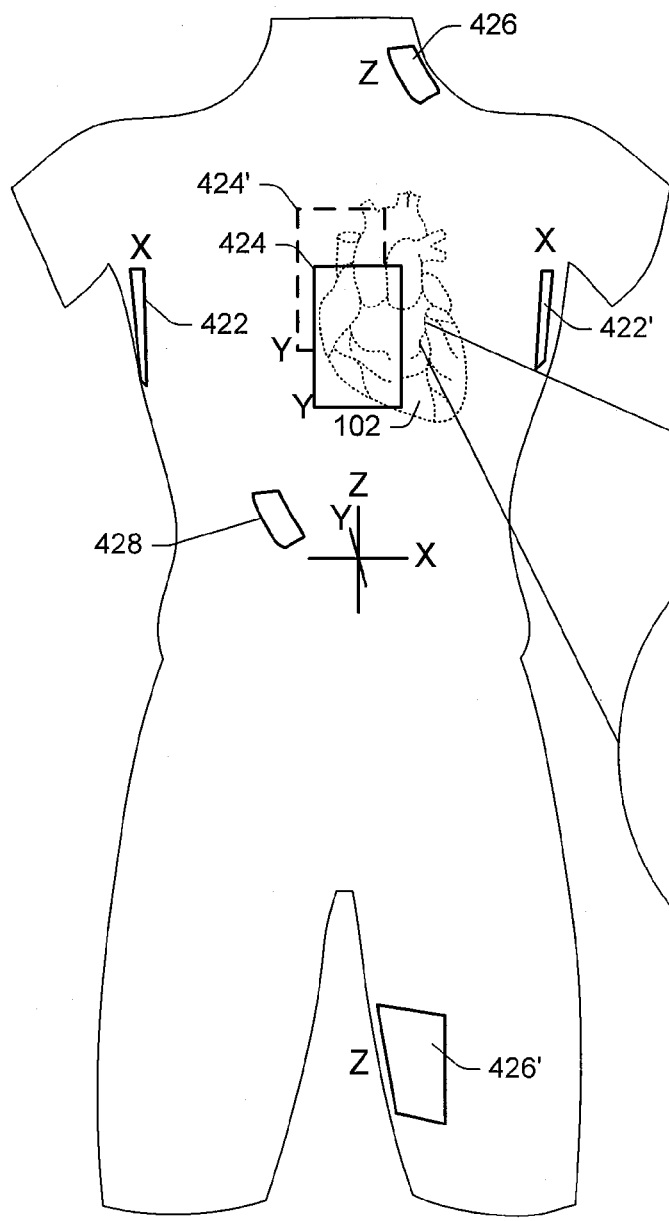
FIG. 4 is an exemplary arrangement of a lead and electrodes for acquiring position information and optionally other information.
Figure 4:
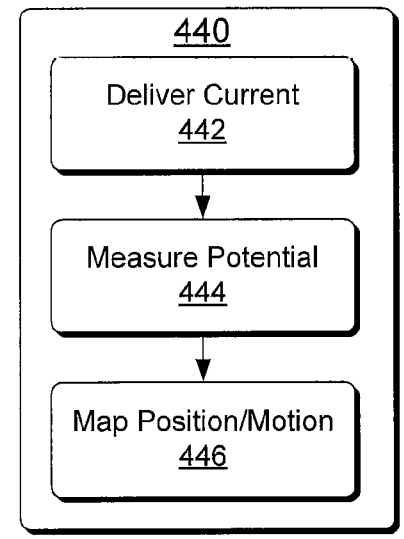
Figure 4:
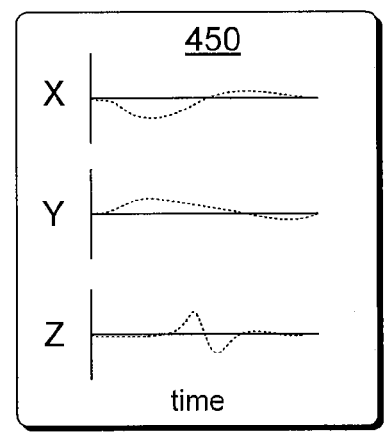

FIG. 4 shows an arrangement and method 400 that may rely in part on a commercially available system marketed as ENSITE® NAVX® localization system (see also LOCAL-ISA® system, Medtronic, Inc., Minnesota). The ENSITE® NAVX® system is a computerized storage and display system for use in electrophysiology studies of the human heart. The system consists of a console workstation, patient interface unit, and an electrophysiology mapping catheter and/or surface electrode kit. By visualizing the global activation pattern seen on color-coded isopotential maps in the system, in conjunction with the reconstructed electrograms, an electrophysiologist can identify the source of an arrhythmia and can navigate to a defined area for therapy. The ENSITE® system is also useful in treating patients with simpler arrhythmias by providing non-fluoroscopic navigation and visualization of conventional electrophysiology (EP) catheters.

As shown in FIG. 4, electrodes 432, 432', which may be part of a standard EP catheter 430 (or lead), sense electrical potential associated with current signals transmitted between three pairs of surface electrode patches 422, 422' (X-axis), 424, 424' (Y-axis) and 426, 426' (Z-axis). An addition electrode patch 428 is available for reference, grounding or other function. The ENSITE® NAVX® system can also collect electrical data from a catheter and can plot a cardiac electrogram from a particular location (e.g., cardiac vein 103 of heart 102). Information acquired may be displayed as a 3-D isopotential map and as virtual electrograms. Repositioning of the catheter allows for plotting of cardiac electrograms from other locations. Multiple catheters may be used as well. A cardiac electrogram or electrocardiogram (ECG) of normal heart activity (e.g., polarization, depolarization, etc.) typically shows atrial depolarization as a "P wave", ventricular depolarization as an "R wave", or QRS complex, and repolarization as a "T wave". The ENSITE® NAVX® system may use electrical information to track or navigate movement and construct three-dimensional (3-D) models of a chamber of the heart.

A clinician can use the ENSITE® NAVX® system to create a 3-D model of a chamber in the heart for purposes of treating arrhythmia (e.g., treatment via tissue ablation). To create the 3-D model, the clinician applies surface patches to the body. The ENSITE® NAVX® system transmits an electrical signal between the patches and the system then senses the electrical signal using one or more catheters positioned in the body. The clinician may sweep a catheter with electrodes across a chamber of the heart to outline structure. Signals acquired during the sweep, associated with various positions, can then be used to generate a 3-D model. A display can display a diagram of heart morphology, which, in turn, may help guide an ablation catheter to a point for tissue ablation.

With respect to the foregoing discussion of current delivery and potential measurement, per a method 440, a system (e.g., such as the ENSITE® NAVX® system) delivers low level separable currents from the three substantially orthogonal electrode pairs (422, 422', 424, 424', 426, 426') positioned on the body surface (delivery block 442) and optionally the electrode 428 (or one or more other electrodes). The specific position of a catheter (or lead) electrode within a chamber of the heart can then be established based on three resulting potentials measured between the recording electrode with respect to a reference electrode, as seen over the distance from each patch set to the recording tip electrode (measurement block 444). Sequential positioning of a catheter (or lead) at multiple sites along the endocardial surface of a specific chamber can establish that chamber's geometry, i.e., position mapping (position/motion mapping block 446). Where the catheter (or lead) 430 moves, the method 440 may also measure motion.

In addition to mapping at specific points, the ENSITE® NAVX® system provides for interpolation (mapping a smooth surface) onto which activation voltages and times can be registered. Around 50 points are required to establish a surface geometry and activation of a chamber at an appropriate resolution. The ENSITE® NAVX® system also permits the simultaneous display of multiple catheter electrode sites, and also reflects real-time motion of both ablation catheters and those positioned elsewhere in the heart.

The ENSITE® NAVX® system relies on catheters for temporary placement in the body. Various exemplary techniques described herein optionally use one or more electrodes for chronic implantation. Such electrodes may be associated with a lead, an implantable device, or other chronically implantable component. Referring again to FIG. 3, the configuration block 310 indicates that intraoperative configurations 312 and chronic configurations 314 may be available. Intraoperative configurations 312 may rely on a catheter and/or a lead suitable for chronic implantation.

With respect to motion, the exemplary system and method 400 may track motion of an electrode in one or more dimensions. For example, a plot 450 of motion versus time for three dimensions corresponds to motion of one or more electrodes of the catheter (or lead) 430 positioned in a vessel 103 of the heart 102 where the catheter (or lead) 430 includes the one or more electrodes 432, 432'. Two arrows indicate possible motion of the catheter (or lead) 430 where hysteresis may occur over a cardiac cycle. For example, a systolic path may differ from a diastolic path. An exemplary method may analyze hysteresis for any of a variety of purposes including selection of a stimulation site, selection of a sensing site, diagnosis of cardiac condition, etc.

The exemplary method 440, as mentioned, includes the delivery block 442 for delivery of current, the measurement block 444 to measure potential in a field defined by the delivered current and the mapping block 446 to map motion based at least in part on the measured potential. According to such a method, motion during systole and/or diastole may be associated with electrical information. Alone, or in combination with electrical information, the mechanical motion information may be used for selection of optimal stimulation site(s), determination of hemodynamic surrogates (e.g., surrogates to stroke volume, contractility, etc.), optimization of CRT, placement of leads, determination of pacing parameters (AV delay, VV delay, etc.), etc.

The system 400 may use one or more features of the aforementioned ENSITE® NAVX® system. For example, one or more pairs of electrodes (422, 422', 424, 424', 426, 426') may be used to define one or more dimensions by delivering an electrical signal or signals to a body and/or by sensing an electrical signal or signals. Such electrodes (e.g., patch electrodes) may be used in conjunction with one or more electrodes positioned in the body (e.g., the electrodes 432, 432').

The exemplary system 400 may be used to track motion of one or more electrodes due to systolic motion, diastolic motion, respiratory motion, etc. Electrodes may be positioned along the endocardium and/or epicardium during a scouting or mapping process for use in conjunction with electrical information. Such information may also be used alone, or in conjunction with electrical information, for identifying the optimal location of an electrode or electrodes for use in delivering CRT. For example, a location may be selected for optimal stimulation, for optimal sensing, or other purposes (e.g., anchoring ability, etc.).

With respect to stimulation, stimulation may be delivered to control cardiac mechanics (e.g., contraction of a chamber of the heart) and motion information may be acquired where the motion information is associated with the controlled cardiac mechanics. An exemplary selection process may identify the best stimulation site based on factors such as electrical activity, electromechanical delay, extent of motion, synchronicity of motion where motion may be classified as systolic motion or diastolic motion. In general, motion information corresponds to motion of an electrode or electrodes (e.g., endocardial electrodes, epicardial electrodes, etc.) and may be related to motion of the heart.

Figure 5:
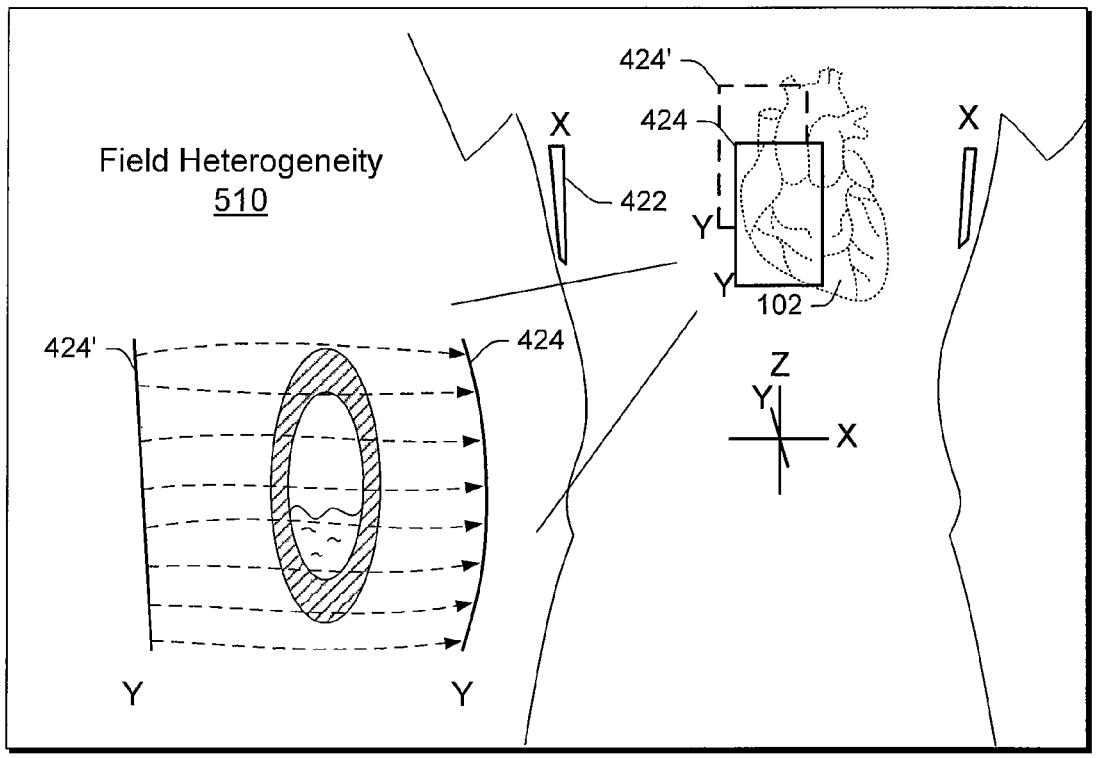
FIG. 5 is a diagram illustrating field heterogeneities associated with current generated fields in the body along with a method to compensate for field heterogeneities.
Figure 5:
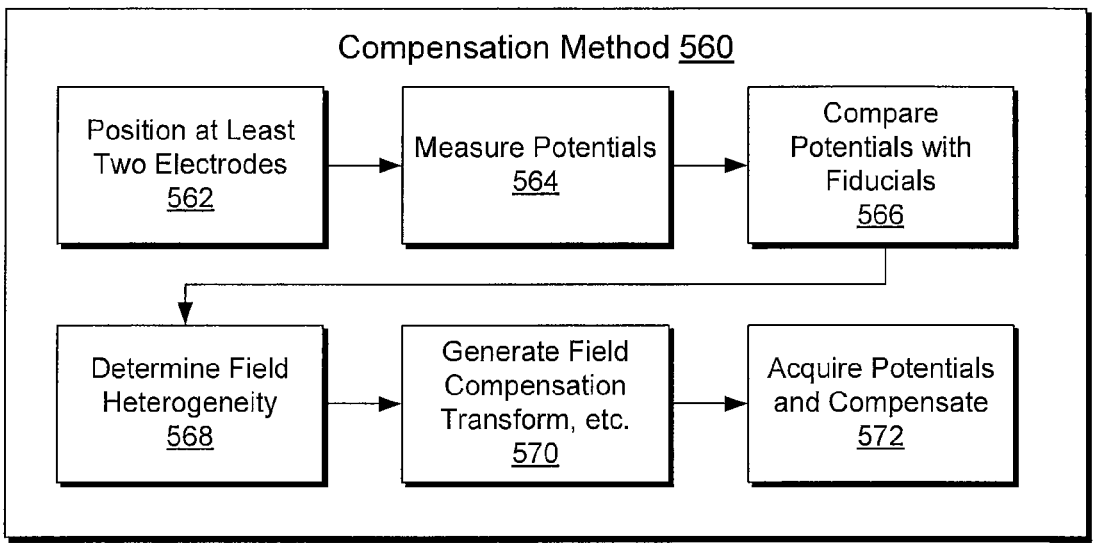

FIG. 5 shows a field compensation scheme 500 for a localization system. As mentioned, the ENSITE® NAVX® system includes a feature known as "field scaling", which may operate according to the scheme 500. As described herein, exemplary electrodes can enhance mapping of field heterogeneities and increase accuracy of position determinations (e.g., via compensation techniques).

A diagram of field heterogeneity 510 shows a cross-section between the Y-axis patches 424, 424'. Internal physiology and accompanying dielectric properties introduce field heterogeneities. Further, as physiology changes with respect to time due to cardiac function, respiration, patient position, etc., heterogeneities vary with respect to time as well.

An exemplary compensation method 560 commences in a positioning block 562 that positions at least two electrodes. A measurement block 564 measures potential for each of the electrodes. A comparison block 566 follows that includes measuring or otherwise providing for a distance or angle between the at least two electrodes. For example, an electrode may be considered a fiducial and spacing between two or more electrodes known a priori. In an alternative example, a lead may have fiducials with known spacing that are visible via x-ray imaging along with the electrodes. In such an example, a clinician may simply count the number of fiducials between electrodes. In yet another example, one or more anatomical features may be relied upon to establish a distance that can be used to infer a distance between two electrodes. Of course, combinations of such techniques may be used.

According to the method 560, a determination block 568 determines whether and to what extent the field is heterogeneous. For example, if a known distance between two electrodes is 5 mm and the current generated field is expected to have a particular field gradient over a distance of 5 mm, then the potentials can be analyzed to determine if the field gradient differs from its expected field gradient. Given an appropriate number of determinations, a generation block 570 generates a field compensation transform, algorithm, map, table or the like. The method 560 then proceeds to an acquisition block 572 that acquires potentials and compensates accordingly for field heterogeneities to provide more accurate position information.

When a localization system is configured to define one or more electrodes as belonging to a single lead or catheter, such a system may display a "tube" that represents the lead body between two electrodes. In the ENSITE® NAVX® system, this display, however, is simply graphical and represented as a straight line, a polynomial, or a spline. As such, it does not truly represent the trajectory or orientation of a lead body in the heart.

As described herein, various exemplary electrodes allow for determination of trajectory or orientation of an electrode, an electrode array, a lead body or a portion of a lead body. Such electrodes can allow a localization system to determine not only the position of an electrode but also its orientation, which can enhance the representation of a lead, enhance computed parameters related to the motion of an electrode or lead, etc.

Figure 6:
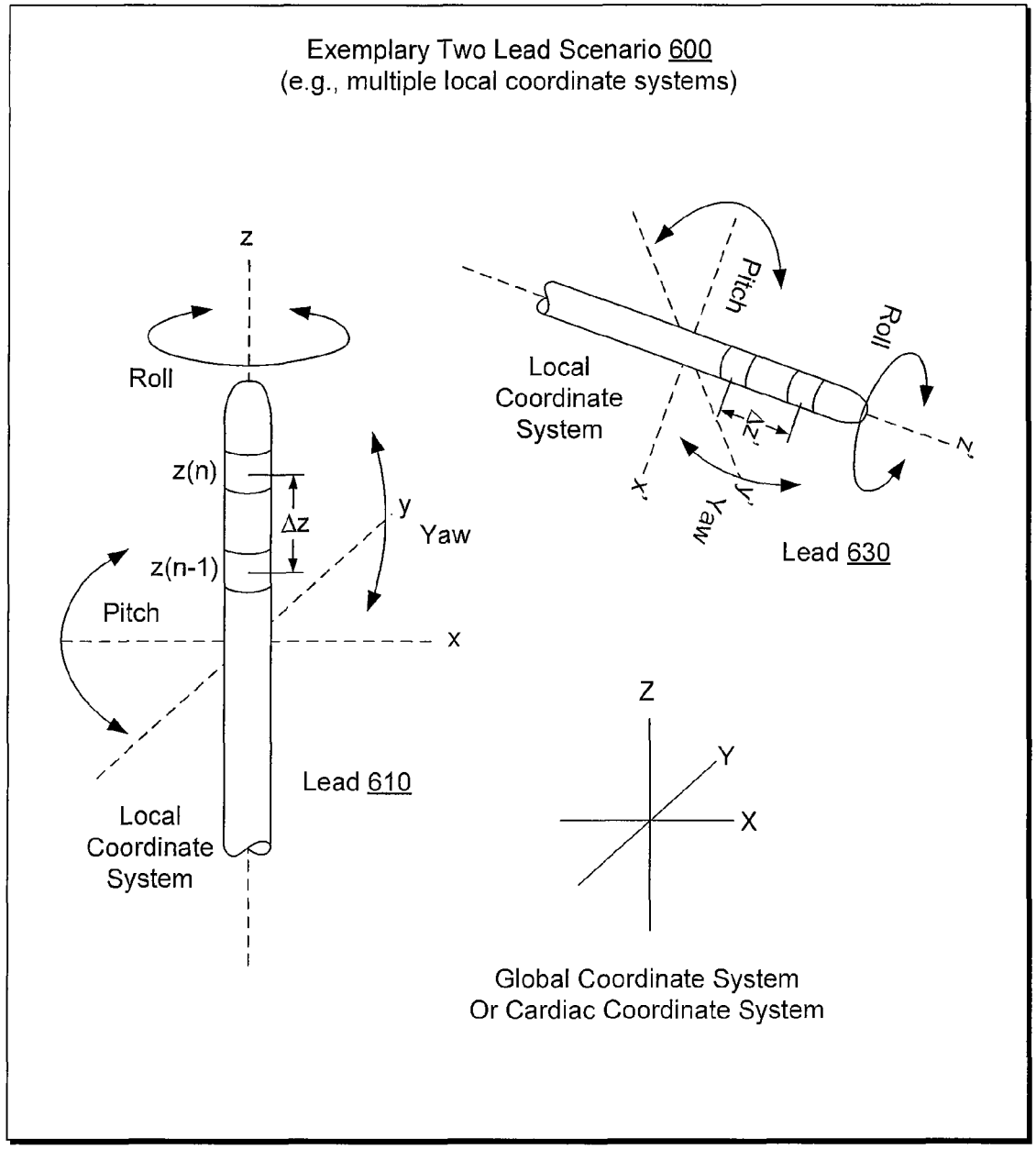
FIG. 6 is a diagram illustrating a two lead scenario with respect to a local coordinate system for each lead and a global coordinate system.

FIG. 6 shows an exemplary two lead scenario 600 along with local coordinate systems for each of the leads 610, 630. In the example of FIG. 6, electrodes on the leads 610, 630 are conventional ring electrodes, which fail to yield rich positional information in the local coordinate systems.

In FIG. 6, the two local coordinate systems (x, y, z and x', y', z' dimensions) are shown along with a global coordinate system (X, Y, Z dimensions). While Cartesian coordinates are shown in the example of FIG. 6, other coordinate systems may be utilized.

The leads 610, 630 include two electrodes defined with respect to a z-axis: z(n) and z(n−1) with a separation of Δz. In the local coordinate systems, the leads 610, 630 may yaw, pitch or roll. Yaw involves rotation about the y-axis, pitch involves rotation about the x-axis and roll involves rotation about the z-axis.

If the lead is viewed as a vehicle in the body, yaw is lateral rotational or oscillatory movement of the vehicle about its vertical axis. Given this vehicle analogy, pitch is movement about an axis that is perpendicular to the vehicle's longitudinal axis and horizontal with respect to its primary body. Pitch attitude is the orientation of the vehicle with respect to the pitch axis. The pitching moment is the rising and falling of the vehicle's nose. When the nose rises, the pitching moment is positive; when the nose drops, the pitching moment is negative and is also called a diving moment. As for roll, it represents motion of the vehicle about its longitudinal, or nose-tail, axis.

The exemplary local coordinate systems approach of FIG. 6 can assist in navigation of a lead in a patient's body. Further, an analogy to vehicle motion facilitates implementation of automated or assisted navigation control (e.g., 3-D robotic control in conjunction with a localization system).

Figure 7:
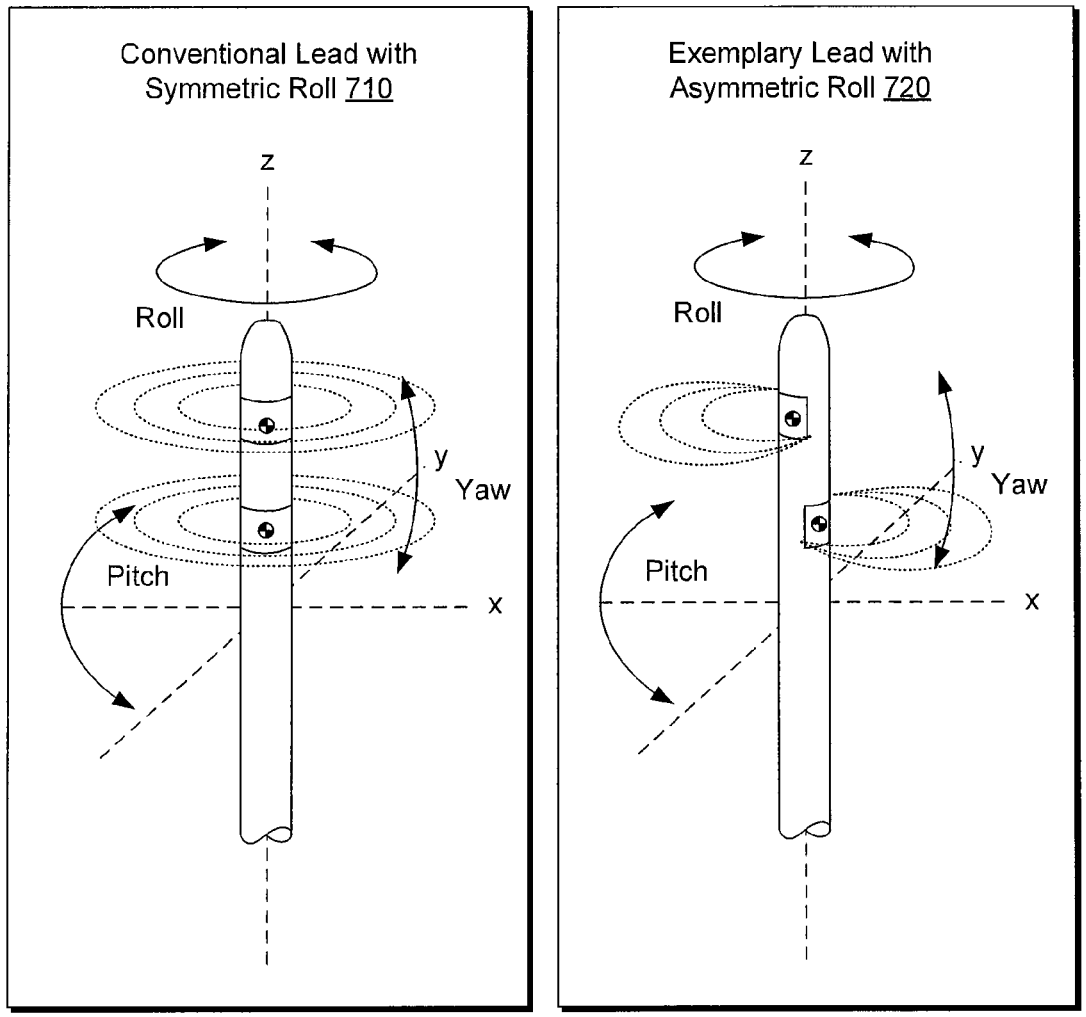
FIG. 7 is a diagram of a conventional lead with symmetric roll in a local coordinate system and an exemplary lead with asymmetric roll in a local coordinate system as well as an exemplary method for using the exemplary lead.
Figure 7:
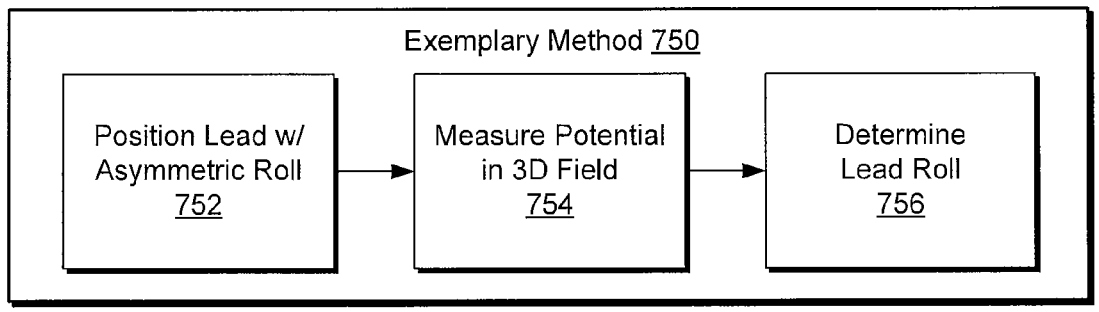

As mentioned, the ring electrodes, having a symmetric axis or rotation about the z-axis cannot readily provide for orientation of the lead 610 or the lead 630. To demonstrate this point, FIG. 7 shows a diagram of a conventional lead with symmetric roll 710 and an exemplary lead with asymmetric roll 720 as well as an exemplary method 750 for using the lead 720. The exemplary lead 720 includes two electrodes that are shaped and positioned like opposing boiler plates but offset along the z-axis. Further, the electrical center of each electrode is offset from the z-axis (e.g., as shown, +/−x-axis). Thus, lead roll causes the electrical centers of the electrodes to move in the x,y-plane, which, given a surrounding field of a localization system, will result in changing positions of the two electrodes (see, e.g., electrical centers in example 930 of FIG. 9).

The exemplary method 750 includes a positioning block 752 where a clinician positions a lead such as the lead 720 in a patient's body. For example, the clinician may position a lead in a patient where the lead has a longitudinal axis that extends from a proximal end to a distal end and where the lead includes an electrode with an electrical center offset from the longitudinal axis of the lead body. After or during positioning, in a measurement block 754, the clinician instructs a localization system to measure electrical potential in a three-dimensional potential field using the electrode. In a determination block 756, a localization system determines, based on measured electrical potential and the offset of the electrical center, lead roll about the longitudinal axis of the lead body (e.g., in degrees, radians, etc.). As described herein, an exemplary method can include displaying a lead roll indicator on a display, for example, where the lead roll indicator indicates degrees of roll about a longitudinal axis of a lead body. Such a method may include positioning an electrode of a lead based at least in part on the determined lead roll (e.g., to be directed toward or away from tissue such as nerve tissue, damaged myocardium, etc.).

Figure 8:
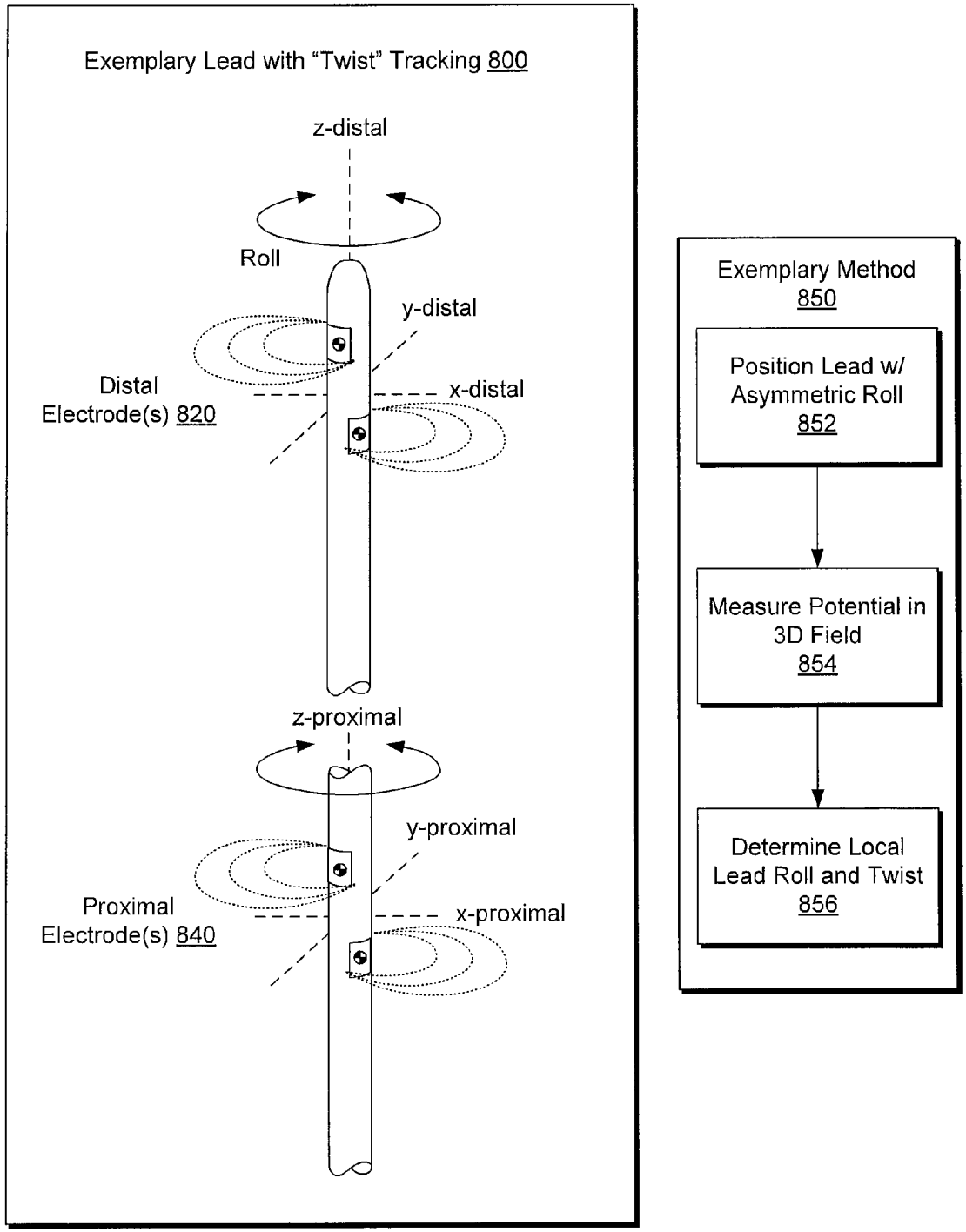
FIG. 8 is a diagram of an exemplary lead with twist tracking features along with an exemplary method for using the exemplary lead.

FIG. 8 shows an exemplary lead 800 with twist tracking features as well as an exemplary method 850 for determining twist. The lead 800 includes a distal pair of electrodes 820 and a proximal pair of electrodes 840. As the lead 800 is resilient, its body may twist such that a roll differential exists between the distal pair 820 and the proximal pair 840. In this example, two local coordinate systems may be defined, one for each of the electrode pairs 820, 840. Even where the lead 800 remains at a particular point in the body (e.g. tip position), rotation or twist may be tracked with respect to a clinician's actions or with respect to body actions or function.

The exemplary method 850 includes a positioning block 852 where a clinician positions a lead such as the lead 800 in a patient's body. For example, the clinician may position a lead in a patient where the lead has a longitudinal axis that extends from a proximal end to a distal end and where the lead includes electrodes where at least two electrodes have an electrical center offset from the longitudinal axis of the lead body. After or during positioning, in a measurement block 854, the clinician instructs a localization system to measure electrical potential in a three-dimensional potential field using the at least two electrodes. In a determination block 856, a localization system determines, based on measured electrical potential and the offsets of the electrical centers, local lead roll and lead twist about the longitudinal axis of the lead body (e.g., in degrees, radians, etc.).

Figure 9:
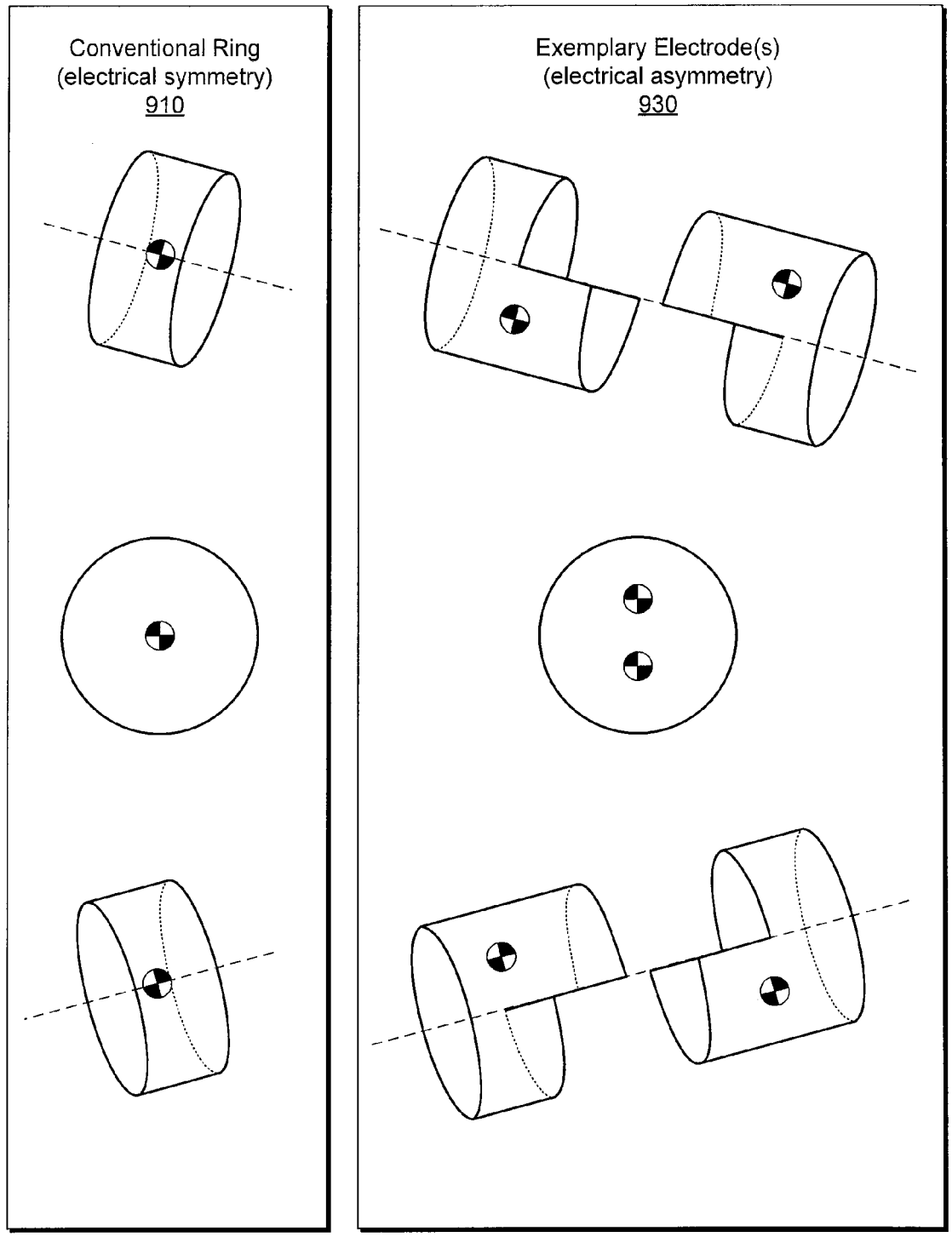
FIG. 9 is a diagram of a conventional ring electrode and its electrical center and a pair of exemplary electrodes and corresponding individual electrical centers.

FIG. 9 shows various views of a conventional ring electrode 910 and an exemplary pair of electrodes 930. These views further demonstrate how electrical centers vary or do not vary with respect to electrode characteristics. As shown, the conventional ring electrode 910 has an electrical center along a central axis of rotation. A view along this axis shows the electrical center of the ring electrode 910 centered such that rotation about the axis does not result in displacement of its electrical center from the axis. Further, rotation of the ring electrode 910 about its geometric center does not result in displacement of its electrical center.

In contrast, each of the individual electrodes of the pair 930 has an electrical center offset from a central axis (e.g., z-axis). A view along this axis shows the two distinct electrical centers. Further rotation about the geometric center of the pair of electrodes 930 results in displacement of each electrical center.

Figure 10:
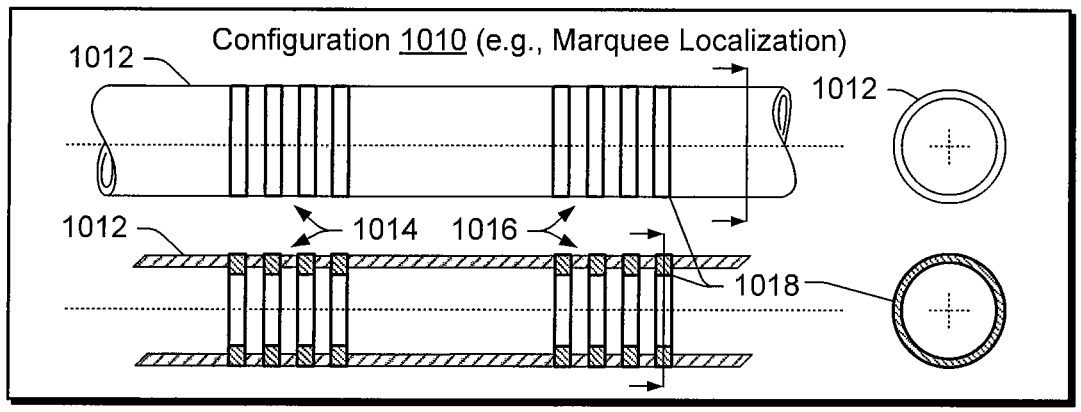
FIG. 10 is a series of diagrams illustrating various exemplary electrodes with respect to a lead body.
Figure 10:
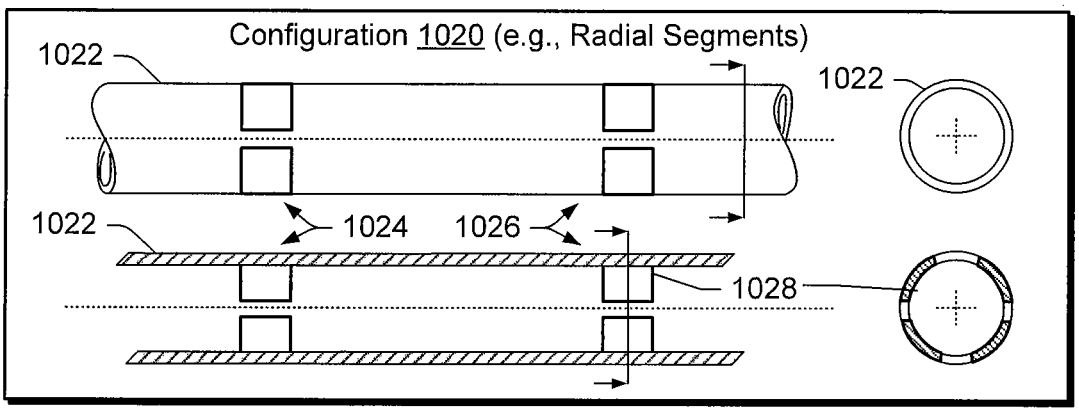
Figure 10:
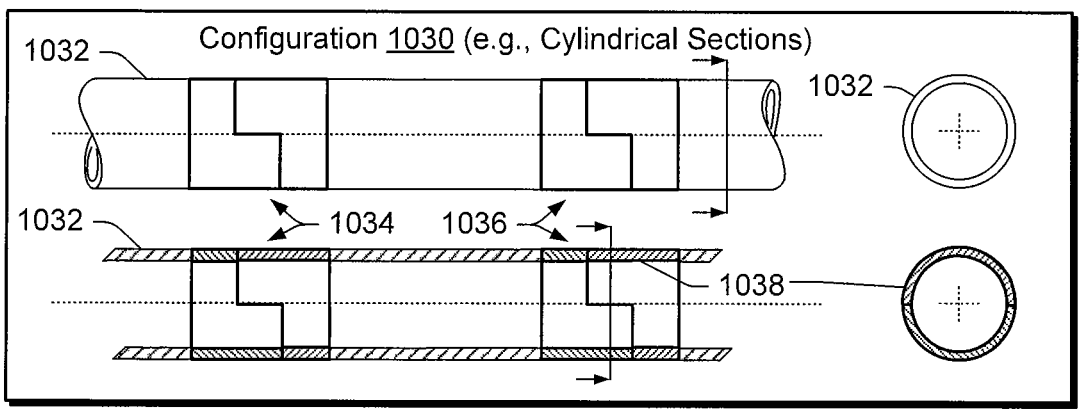
Figure 11:
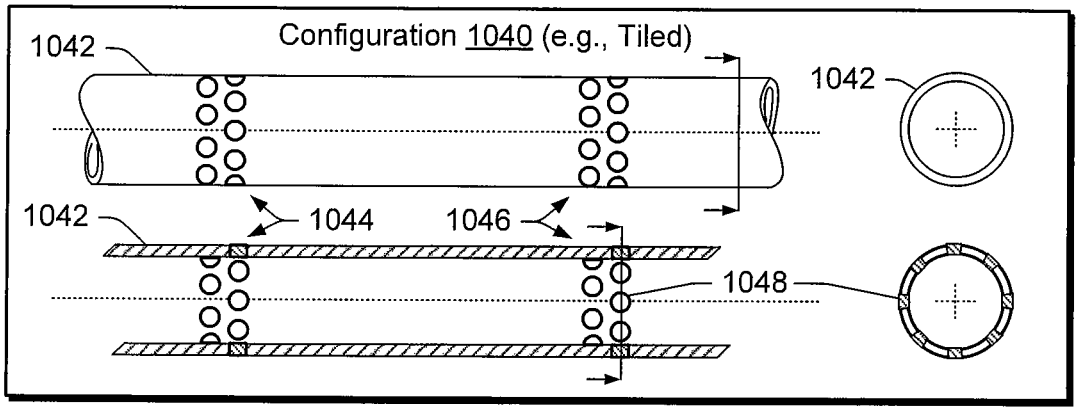
FIG. 11 is a series of diagrams illustrating various exemplary electrodes with respect to a lead body.
Figure 11:
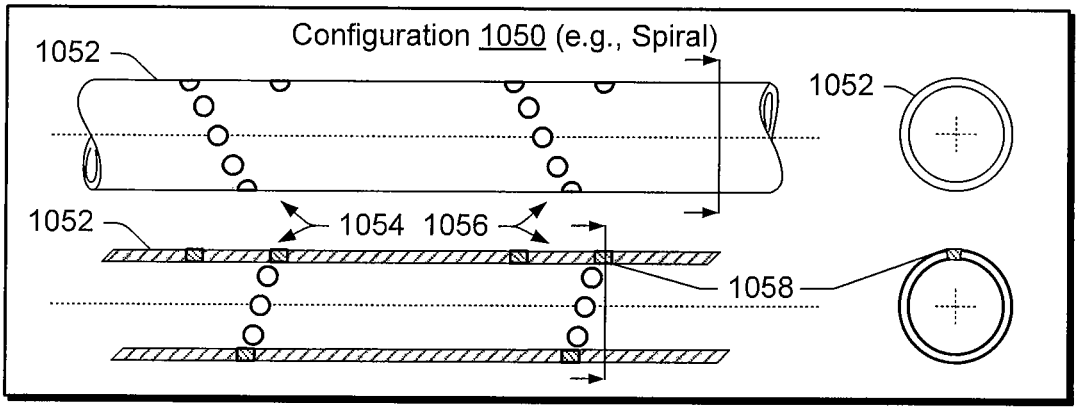

Given the foregoing discussion of coordinate systems and electrical centers, various exemplary electrodes are shown in FIGS. 10 and 11 as being part of a lead. Specifically, FIG. 10 shows exemplary electrode configurations 1010, 1020, and 1030 and FIG. 11 shows exemplary electrode configurations 1040 and 1050. Such arrangements may include one or more circuits such as the circuit 168 of the lead 160 of FIG. 1 (e.g., to select or otherwise control an electrode configuration).

The configuration 1010 includes a lead body 1012 and two series of electrodes 1014, 1016 where each series includes individually selectable ring electrodes 1018. Each of the series of electrodes 1014, 1016 may be formed by splitting, perpendicular to the lead body axis, a single electrode such that it resembles two or more rings arranged end-to-end lengthwise.

The configuration 1010 may be used as a marquee whereby a localization system successively displays a position for each individual ring in a series. Thus, the display would appear as a moving sequence of dots or the like progressing along the axis of the lead body 1012 (e.g., a successive series of markers). When the direction is known (e.g., from proximal to distal), a clinician can readily ascertain the orientation of the lead body 1012. Further, the localization system may display colors or other indicia to indicate a corresponding direction (e.g., vector). For example, a red vector may indicate a direction "into" a display pane (e.g., away from an observer) while a blue vector may indicate a direction "out of" a display pane (e.g., toward an observer). Yet further, where the series 1014, 1016 are spaced at some distance, the localization system may display colors or other indicia to same or opposing directions. As described herein, an exemplary method may include altering a color of the lead direction marquee, for example, based on direction of the lead direction marquee with respect to a coordinate system (e.g., a coordinate system that corresponds to physiology of the heart, a patient's body, etc.).

The configuration 1020 includes a lead body 1022 and two series of electrodes 1024, 1026 where each series includes individually selectable arc section electrodes 1028. Each of the series of electrodes 1024, 1026 may be formed by splitting a single electrode such that it resembles two or more arced sections arranged circumferentially. For example, the lead 160 of FIG. 1 includes electrodes 163, which are arranged circumferentially about a lead body. As mentioned, various exemplary leads may include one or more circuits for control of one or more electrodes in an electrode array (see, e.g., the circuit 168 of the lead 160 of FIG. 1).

The configuration 1030 includes a lead body 1032 and two sets of electrodes 1034, 1036 where each set includes individually selectable cylindrical section electrodes 1038. Each set of electrodes 1034, 1036 may be formed by splitting a single electrode such that it resembles two cylindrical sections with an axial offset along the split boundary. Such an electrode set was described with respect to FIG. 9 (see electrodes 930), specifically to explain electrical centers. As shown in FIG. 10, each set has circumferential and axial features. In a particular example, each set 1034, 1036 can include two or more interlocking pieces that can form a complete ring, which may be referred to as an interlocking arrangement.

The configuration 1040 includes a lead body 1042 and two sets of electrodes 1044, 1046 where each set includes individually or group selectable electrodes 1048 arranged circumferentially. Each set of electrodes 1044, 1046 is optionally formed by a group of conductors where each conductor is attached to or forms an exposed end surface along the lead body 1042 arranged circumferentially that, when taken together, resemble a ring. In FIG. 11, the configuration 1040 may be referred to as a tiled arrangement.

The configuration 1050 includes a lead body 1052 and two sets of electrodes 1054, 1056 where each set includes individually or group selectable electrodes 1058 arranged circumferentially and axially in a helix or spiral fashion. Each set of electrodes 1054, 1056 is optionally formed by a group of conductors where each conductor is attached to or forms an exposed end surface along the lead body 1052 arranged circumferentially and axially that, when taken together, resemble a ring. In FIG. 11, the configuration 1050 may be referred to as a spiral arrangement.

In the examples of FIGS. 10 and 11, the electrode sets may be (e.g., for purposes of cardiac study and therapy), approximately 0.3 mm to approximately 4.0 mm in diameter and approximately 0.5 mm to approximately 2.5 mm in length.

Figure 12:
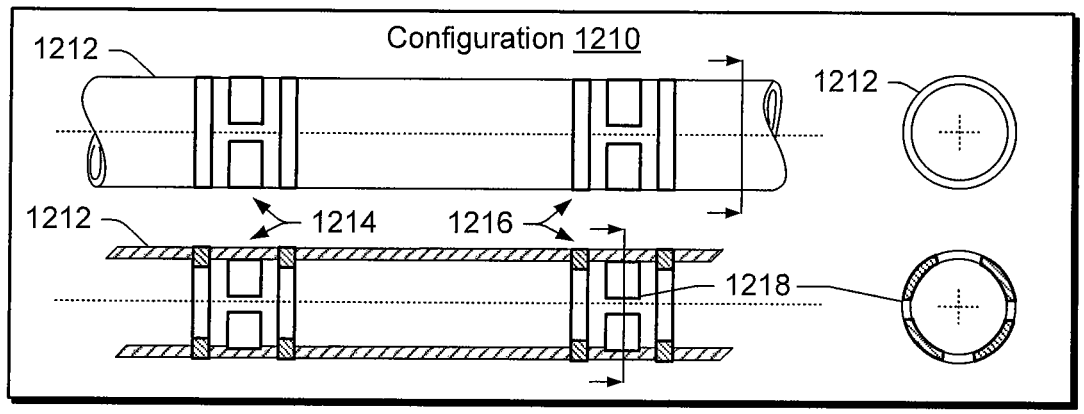
FIG. 12 is a series of diagrams illustrating various exemplary electrodes with respect to a lead body.
Figure 12:
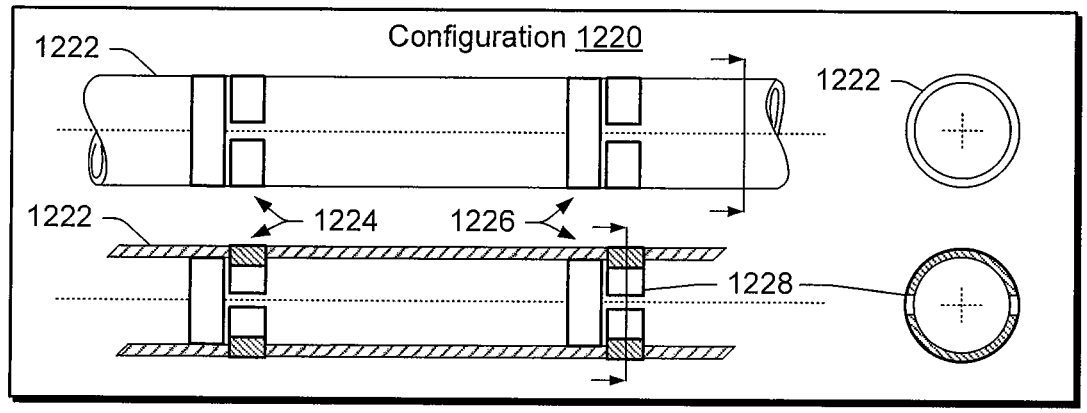

FIG. 12 shows exemplary electrodes configurations 1210, 1220, which are suitable for determination of local field heterogeneities. The configurations 1210, 1220 include one or more split-ring electrodes. As described herein, a circumferential arrangement or a combination of circumferential and axial arrangements are particularly suited to determining local field heterogeneities.

The configuration 1210 includes a lead body 1212 and two sets of electrodes 1214, 1216 where each set includes individually or group selectable electrodes arranged circumferentially and axially. Each set of electrodes 1214, 1216 has one or more associated conductors for electrodes of proximal, middle, and distal portions. In the example of FIG. 12, the proximal and distal portions cover the complete circumference of the lead body 1212 and the middle portion (e.g., portion 1218) is subdivided into three or more portions about the circumference of the lead body 1212.

The configuration 1220 includes a lead body 1222 and two sets of electrodes 1224, 1226 where each set includes individually or group selectable electrodes arranged circumferentially and axially. Each set of electrodes 1224, 1226 has one or more associated conductors for electrodes of proximal and distal portions. In the example of FIG. 12, the proximal and distal portions are subdivided in two or more circumferential portions that are staggered with respect to one another (see, e.g., cross-section of electrode 1228).

As described herein, since distance between electrode portions in each direction in local lead or catheter coordinates is known and typically fixed, the corresponding distance measured in localization system coordinates (e.g., ENSITE® NAVX® system 3D field coordinates) can be used to define a local field scaling factor.

Figure 13:
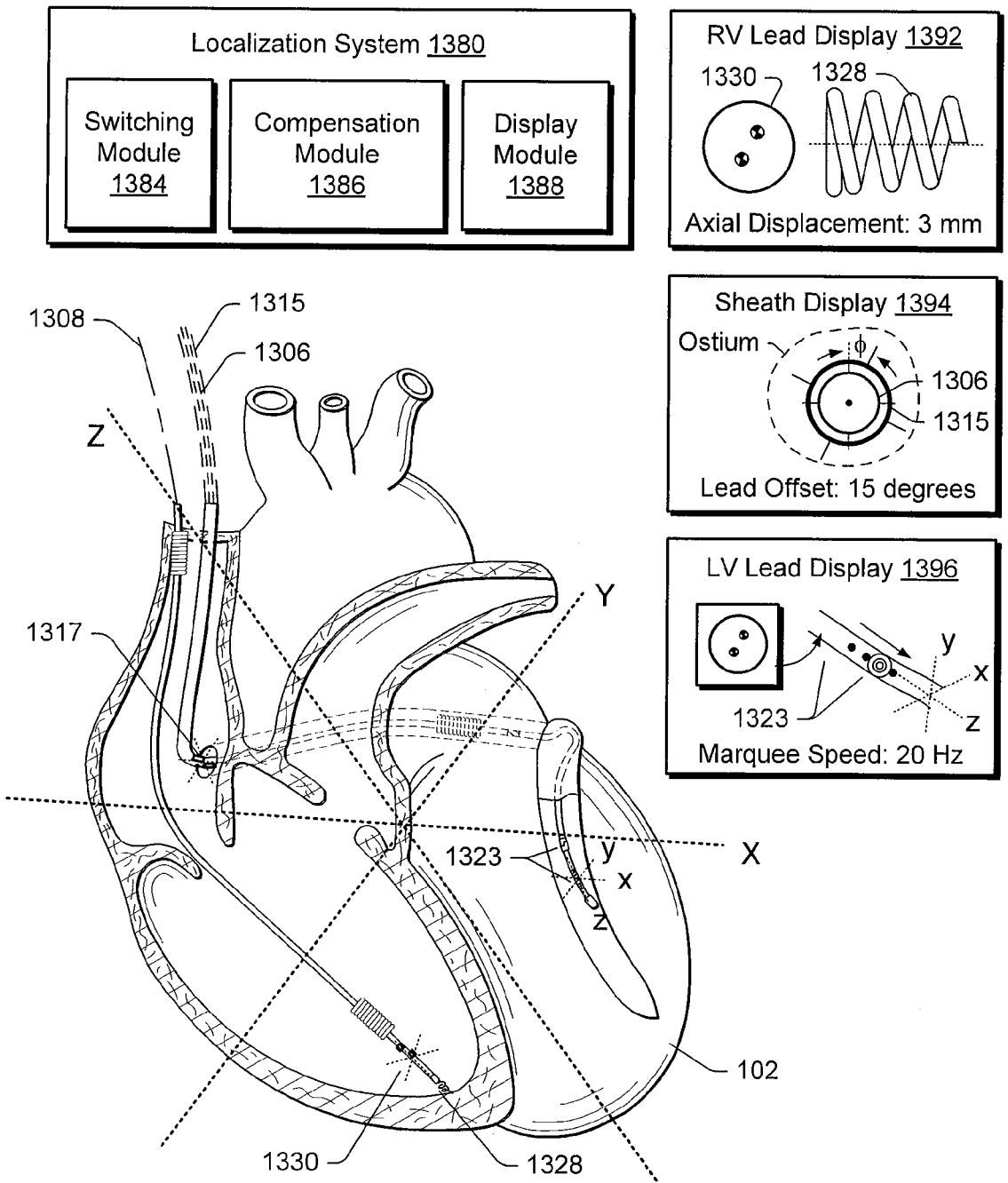
FIG. 13 is a diagram of an exemplary localization system, exemplary arrangement of leads in the heart and exemplary displays.

FIG. 13 shows various exemplary methods and displays using a localization system 1300. The heart 102 is shown with a right ventricular lead 1308 and a left ventricular lead 1306 with a guidance catheter 1315. The right ventricular lead 1308 includes a pair of electrodes 1330 having electrical centers offset from a longitudinal axis of the lead body and a tip electrode with a screw or helix 1328 for attachment to the myocardium. The left ventricular lead includes a series of electrodes 1323 with a combination of marquee electrodes (see, e.g., electrodes 1010 of FIG. 10) and interlocking electrodes (see, e.g., electrodes 1030 of FIG. 10).

In the example of FIG. 13, a catheter or sheath 1315 is used for placement of the left ventricular lead 1306. The catheter 1315 includes a pair of electrodes 1317 having electrical centers offset from a longitudinal axis of the catheter 1315.

A localization system 1380 is configured via a switching module 1384 to acquire information from the various electrodes, configured via a compensation module 1386 to compensate for field heterogeneity and configured via a display module 1388 to generate data suitable for display on a monitor, screen, etc. As described herein, a localization system may include an integral display (e.g., as part of a console or notebook like arrangement) or may include memory to store data suitable for display (e.g., in a graphics buffer). A localization system typically includes one or more graphics processors (e.g., a graphics accelerator card, display adapter, etc.) configured for generating multidimensional graphics data that can be rendered on a display for viewing by a clinician. Communication between a localization system and a display may occur via wire or wirelessly or via a combination of both wire and wireless communication. Data may also be stored to a storage device and then loaded to a system for display. The display module 1388 includes software or hardware and software for generating data suitable for display on a monitor, screen, etc.

An exemplary RV lead display 1392 based on data generated by the display module 1388 shows a graphic of electrical centers of the electrodes 1330 with respect to the tip electrode screw 1328. Insertion of the tip electrode screw 1328 may be achieved in any of a variety of manners. For example, a stylet may be inserted in a lumen of the RV lead 1308 and rotated to rotate the tip electrode screw 1328 (e.g., clockwise, counter-clockwise or both clockwise and counter-clockwise). In such an example, the electrodes 1330 may be tracked to determine if the RV lead 1308 is rotating as the stylet is rotated. Further, the localization system 1380 may track the axial distance (e.g., in a local coordinate system) between the electrodes 1330 and the tip electrode screw 1328 as the tip electrode screw 1328 is inserted into the myocardium. The display 1392 may indicate the axial distance as a displacement that a clinician may track during an implant procedure.

An exemplary sheath display 1394 based on data generated by the display module 1388 shows an angle of rotation offset between the catheter or sheath 1315 and the LV lead 1306. The display 1394 also shows an outline of the ostium of the coronary sinus as an anatomical reference for a clinician. In such an example, a clinician may seek to avoid binding of the LV lead 1306 in the sheath 1315 as the LV lead 1306 is positioned in a vein. Such a display can track total rotation (e.g., beyond 360 degrees) and account for positive and negative rotation whether stemming from the sheath 1315 or the LV lead 1306. In the example of FIG. 13, the rotation of the LV lead 1306 may be inferred by information acquired via the series of electrodes 1323 or other electrodes or proximal end information (e.g., an end manipulated by a clinician) or a combination of such aforementioned information.

An exemplary LV lead display 1396 based on data generated by the display module 1388 shows a marquee for the series of electrodes 1323 along with a rotation graphic. In combination, a clinician can readily ascertain direction and orientation of the distal portion of the lead 1306. In the example of FIG. 13, the display 1396 includes a marquee speed indicator, which may correspond to a sampling speed for all or certain electrodes of the series 1323. The localization system 1380 may be configured to receive input from a clinician to control the marquee speed, which can facilitate placement of a lead (e.g., to coordinate with speed or timing of a clinician's hand or control movements).

In the example of FIG. 13, the display 1396 pertains to navigating a lead in a secondary or tertiary branch of the coronary venous system (e.g., tributaries to the coronary sinus). As described herein, the exemplary display 1396 may be applied for display of orientation of a lead or catheter tip, for example, while delivering an active fixation lead or while ablating cardiac or other tissue.

As described herein, an exemplary method can acquire position information using an exemplary lead and determine instantaneous tangent direction along the lead. Such information may be used to accurately render representations of lead bodies on a localization system monitor. In various situations, instantaneous tangent direction along a lead body may be used to determine local myocardial performance (e.g., for CRT optimization).

With respect to a lead that includes a helix (e.g., as an anchoring screw or mechanism), a keyed-tip stylet or a "helix extender" tool (e.g., a piece that clips onto proximal pin and rotates) may be used to deploy a helix without rotating a lead. Alternatively, a lead could be rotated if a helix portion were already extended, for example, to screw a fixed helix into tissue. Various active-fixation leads include a helix that can extend and retract. An exemplary arrangement can include a lead body with an electrode having an electrical center offset from the longitudinal axis of the lead body, which would allow for determinations as to orientation of the lead body. An exemplary arrangement may include a marquee array to determine how far a helix has been extended (e.g., where the further the helix is extended, the more distal the electrical center has moved from another electrode on a known location near the distal portion of the lead, for example, an active "mapping collar"). For a helix that rotates, either independently during deployment or as part of the overall lead rotation of a fixed-helix lead, an exemplary arrangement may allow for an electrical center of the helix to be slightly offset from the longitudinal axis due to the fact that the most distal "turn" of the helix comes to a point and does not complete 360 degrees. While such a offset of an electrical center may be small, a localization system may have sufficient resolution and accuracy to distinguish the offset (e.g., optionally differentially with respect to from a full cylindrical marker).

Figure 14:
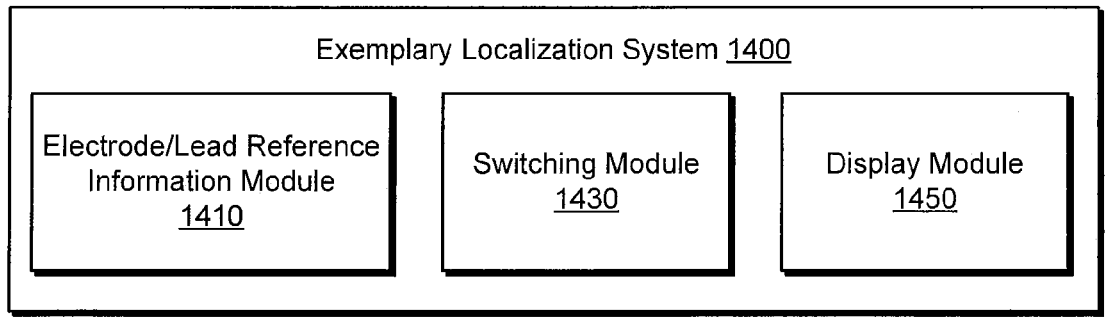
FIG. 14 is a diagram of an exemplary localization system, an exemplary method and an exemplary sequence of data entry.
Figure 14:
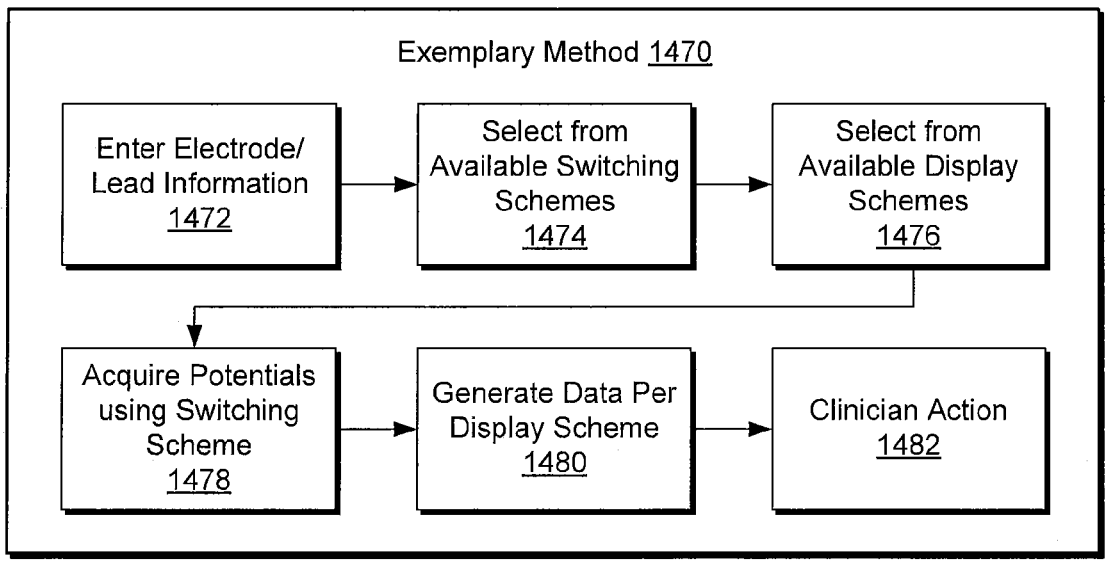
Figure 14:
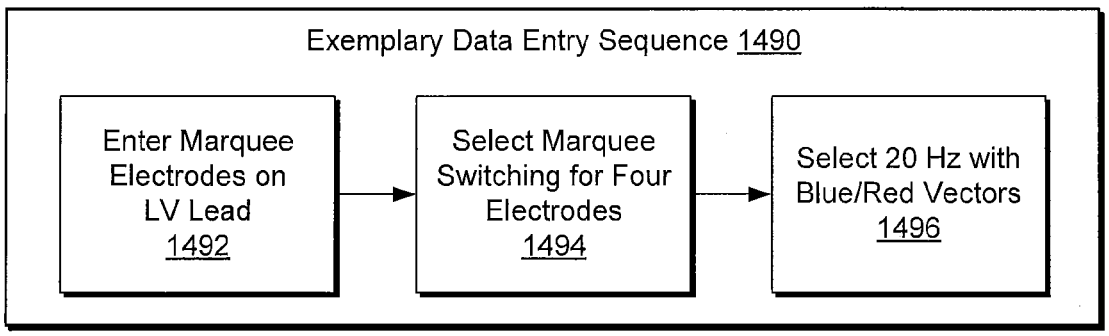

FIG. 14 shows an exemplary localization system 1400, an exemplary method 1470 and an exemplary data entry sequence 1490. The localization system 1400 includes an electrode/lead reference information module 1410, a switching module 1430 and a display module 1450. The module 1410 may access one or more databases that contain information as to electrodes, leads, combinations of leads and electrodes suitable for use with features of the localization system 1400.

Specifically, the localization system 1400 may access information about a lead and determine, based on characteristics of the lead, how the lead may be used with respect to various hardware, software or hardware and software features of the localization system 1400. The module 1410 may include instructions to identify a lead and its electrode type or types upon connection to the localization system 1400. Such a process may be referred to as lead or electrode discovery and can rely on information such as impedance, resistance, number of conductors, a lead's built in circuitry (e.g., an ASIC), etc.

In the example of FIG. 14, the switching module 1430 provides various types of switching schemes, which may be suited to particular characteristics of a lead or electrodes, including the type of clinical procedure. For example, as described with respect to FIG. 13, a screw in procedure for anchoring a lead (see, e.g., RV lead display 1392) is different than a navigation procedure (see, e.g., LV lead display 1396). Thus, the switching module 1430 may include a table or other data structure or algorithm that associates various factors to present suitable switching schemes for user selection. Alternatively, the switching module 1430 may automatically select a switching scheme given information about a lead and its electrodes.

The display module 1450 includes various algorithms for generating data suitable for display. In the example of FIG. 14, the localization system 1400 may select a display algorithm based on a selected switching scheme. For example, given a switching scheme for anchoring, the display module 1450 may select an algorithm that generates data for display of a myocardial boundary and a screw. As position information is acquired, the module 1450 may update the location and rotational position of the screw with respect to the myocardial boundary.

The exemplary method 1470 may be implemented using a localization system with the modules 1430 and 1450. The method 1470 commences in an entry block 1472 where electrode/lead information is entered, for example, per the various manners discussed above. In a particular example, a clinician may enter such information via an input device (e.g., keyboard, touch screen, microphone, mouse, etc.). In a selection block 1474, a clinician selects an appropriate switching scheme from one or more available switching schemes. In another selection block 1476, the clinician selects an appropriate display scheme from one or more available display schemes. The order of the blocks 1474 and 1476 may be reversed or may occur simultaneously (e.g., where display infers switching or where switching infers display).

Once appropriate information has been entered and selections made, the method 1470, in an acquisition block 1478, acquires potentials using the electrodes according to the selected switching scheme. A generation block 1480 follows that generates data based on the acquired potentials according to the selected display scheme. Upon display of the data, along with corresponding graphics, in an action block 1482, a clinician may take appropriate actions. For example, a clinician may navigate the lead, anchor a lead, conduct tests, etc.

The exemplary data entry sequence 1490 demonstrates how and the type of information a clinician may enter while using a localization system operating according to the method 1470. In first entry block 1492, a clinician enters information to notify the localization system that a series of marquee electrodes will be used on a LV lead. In a second entry block 1494, the clinician selects a switching scheme for four marquee electrodes. In a third entry block 1496, the clinician selects a display scheme that will display the marquee with an electrode-to-electrode frequency of 20 Hz (e.g., marquee display rate) and with blue and red vectors or colors to indicate whether the marquee is "pointing" out of the display screen or into the display screen.

As described herein, switching may not be required depending on how electrodes of a lead are configuration for electrical connection to a localization system. Further, an exemplary lead may include a data acquisition system and communication system that can communicate acquired data via a data bus, which may be wired or wireless. For example, a lead may include a head-end (e.g., proximal end) A/D, data buffer and communication circuit that can communicate acquired potential data to a localization system. In such an example, the localization system merely receives the data and displays the data according to an appropriate display scheme.

In various examples, a connection scheme exists where electrodes of a lead are electrically connected via one or more conductors to a localization system. For example, a particular arrangement may include independent conductors connected to each portion of a split-ring electrode where each of the conductors is connected to a separate channel of a localization system.

A localization system can include a module for setup where an electrode arrangement is defined as axial, circumferential, interlocking, tiled, etc. and position of any composite electrode (e.g., ring, spiral or other) may be optionally computed and displayed as an average of each of its constituent electrode portions. Enhanced tracking features may be computed by a module by combining appropriate signals in sequence.

In another exemplary connection scheme, each portion of a split-ring electrode arrangement has an independent conductor, each of which is connected to a multiplexing unit (MUX), the output of which connects to a single channel of a localization system. The multiplexing unit may (e.g., via software, hardware or hardware and software) combine various electrodes or electrode portions and transmit one or more resultant signals to a localization system. In such a scheme, signals transmitted to the localization system may be perceived as only a single electrode (e.g., where some form of enhanced tracking has already been embedded by the multiplexing unit).

In another exemplary connection scheme, portions of a split-ring electrode arrangement are connected distally by a chip (e.g., chip-based circuitry such as an ASIC) that performs the multiplexing and a single conductor carries the signal to a connection with the localization system. In this example, the chip carries out the switching scheme, as appropriate, for desired enhanced localization functionality.

In another exemplary connection scheme, all portions of a split-ring electrode arrangement are connected to terminals of a multi-terminal hardware switch such as a reed switch or some other electrically, magnetically, or mechanically activated switch. In such an arrangement, an additional patch or other device connected to a localization system can activate the switch sequentially to achieve the desired enhanced function.

With respect to exemplary switching schemes, a scheme can be programmed to constantly track a distal-most electrode of an arrangement of electrodes and sequentially join (e.g., in series) other electrodes of the arrangement, one or more at a time, from proximal to distal. For example, in an axial arrangement containing five electrodes, where the most distal electrode is denoted "A" and the most proximal electrode is denoted "E", a switching scheme may select the following electrode combinations: "AE-AD-AC-AB-AE-AD-AC-AB" Alternatively, the most distal need not always be switched on, but rather simply switch sequentially from most proximal to most distal, for example: "E-D-C-B-A-E-D-C-B-A . . . . " Alternatively, the distal electrode may be always switched on, and the scheme programmed to simply turn one or more proximal electrodes on and off sequentially, for example: "AB-A-AB-A-AB-A . . . . " Such a scheme generates an effect of moving the "center of gravity" of the electrode arrangement from proximal to distal. Information acquired according to such a scheme may be displayed on a monitor as an electrode travelling slightly from proximal to distal along the axial direction (e.g., a marquee effect).

Various exemplary schemes can with electrodes at or near the distal end of a lead can distinguish whether the distal end is pointed tangential or perpendicular to the heart surface, for example, where a localization system is used to fix a lead at a particular location (such as HIS bundle). Further, such a scheme can determine which direction a lead or catheter is pointed as it reaches a branch point in the coronary venous system. With respect to pacing therapies, such an approach can aid sub-branch selection in placement of a pacing lead.

An exemplary scheme can track electrodes of a lead that are located along a lead body (e.g., at a distance from a distal end of more than a centimeter) to more accurately determine the trajectory of the lead body. For example, based on direction that an electrode is pointing, a localization system can use not only the position but also tangent direction in a polynomial or spline calculation to draw a representation of the lead body. An exemplary method can track changes in direction throughout a cardiac cycle to yield valuable information about cardiac rotation. Such information may be used for CRT optimization.

Various exemplary techniques described herein may be applied to scenarios where other types of imaging leads or catheters are used (e.g., fiber-optic, ultrasound, or other modalities). For example, in such a scenario, a localization system can acquire information and determine what direction an imaging lead is pointing, which can help to optimize image acquisition. Such techniques can aid imaging modalities that rely on Doppler methods or backscatter, especially those that may require parallel or perpendicular orientations for the most accurate results.

As described herein, various exemplary electrodes may be used to determine local deformation gradient. For example, a circumferential or interlocking arrangement may be used with an independent-channel connection to a localization system to acquire information for observation of motion as to local deformation. In contrast, for a single, solid electrode, only the extent of average motion in the (x,y,z) Cartesian field can be determined. By observing differential motion of each portion of an exemplary electrode arrangement, not only (x,y,z) components but also rotation about the lead axis and tilt of the catheter axis can be determined. Such detailed motion information can be plugged into a deformation tensor computed for tissue next to the electrode arrangement, yielding valuable information about the local tissue mechanical performance. Such information can be used in conjunction with various CRT optimization schemes.

Exemplary External Programmer

Figure 15:
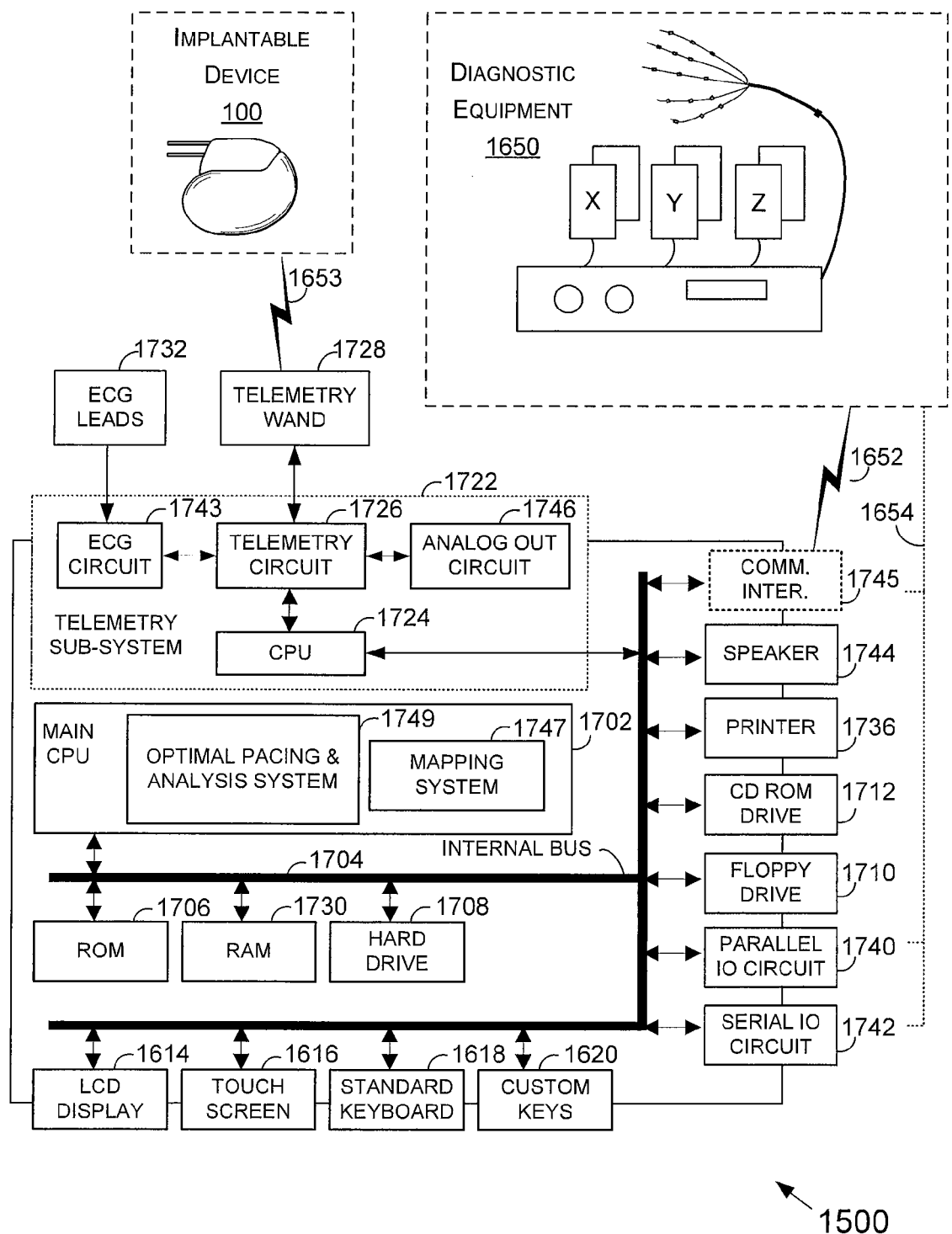
FIG. 15 is an exemplary system for acquiring information and analyzing such information.

FIG. 15 illustrates pertinent components of an external programmer 1500 for use in programming an implantable medical device 100 (see, e.g., FIGS. 1 and 2). The external programmer 1500 optionally receives information from other diagnostic equipment 1650, which may be a computing device capable of acquiring motion information related to cardiac mechanics. For example, the equipment 1650 may include a computing device to deliver current and to measure potentials using a variety of electrodes including at least one electrode positionable in the body (e.g., in a vessel, in a chamber of the heart, within the pericardium, etc.). Equipment may include a lead for chronic implantation or a catheter for temporary implantation in a patient's body. Equipment may allow for acquisition of respiratory motion and aid the programmer 1500 in distinguishing respiratory motion from cardiac.

Briefly, the programmer 1500 permits a clinician or other user to program the operation of the implanted device 100 and to retrieve and display information received from the implanted device 100 such as IEGM data and device diagnostic data. The programmer 1500 may also instruct a device or diagnostic equipment to deliver current to generate one or more potential fields within a patient's body where the implantable device 100 may be capable of measuring potentials associated with the field(s).

The external programmer 1500 may be configured to receive and display ECG data from separate external ECG leads 1732 that may be attached to the patient. The programmer 1500 optionally receives ECG information from an ECG unit external to the programmer 1500. The programmer 1500 may use techniques to account for respiration.

Depending upon the specific programming, the external programmer 1500 may also be capable of processing and analyzing data received from the implanted device 100 and from ECG leads 1732 to, for example, render diagnosis as to medical conditions of the patient or to the operations of the implanted device 100. As noted, the programmer 1500 is also configured to receive data representative of conduction time delays from the atria to the ventricles and to determine, therefrom, an optimal or preferred configuration for pacing. Further, the programmer 1500 may receive information such as ECG information, IEGM information, information from diagnostic equipment, etc., and determine one or more metrics for optimizing therapy.

Considering the components of programmer 1500, operations of the programmer are controlled by a CPU 1702, which may be a generally programmable microprocessor or microcontroller or may be a dedicated processing device such as an application specific integrated circuit (ASIC) or the like. Software instructions to be performed by the CPU are accessed via an internal bus 1704 from a read only memory (ROM) 1706 and random access memory 1730. Additional software may be accessed from a hard drive 1708, floppy drive 1710, and CD ROM drive 1712, or other suitable permanent or removable mass storage device. Depending upon the specific implementation, a basic input output system (BIOS) is retrieved from the ROM 1706 by CPU 1702 at power up. Based upon instructions provided in the BIOS, the CPU 1702 "boots up" the overall system in accordance with well-established computer processing techniques.

Once operating, the CPU 1702 displays a menu of programming options to the user via an LCD display 1614 or other suitable computer display device. To this end, the CPU 1702 may, for example, display a menu of specific programming parameters of the implanted device 100 to be programmed or may display a menu of types of diagnostic data to be retrieved and displayed. In response thereto, the clinician enters various commands via either a touch screen 1616 overlaid on the LCD display or through a standard keyboard 1618 supplemented by additional custom keys 1620, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

With regard to mapping of metrics (e.g., for patterns of conduction), the CPU 1702 includes a 3-D mapping system 1747 and an associated data analysis system 1749. The systems 1747 and 1749 may receive position information and physiological information from the implantable device 100 and/or diagnostic equipment 1650. The data analysis system 1749 optionally includes control logic to associate information and to make one or more conclusions based on metrics, for example, as indicated in FIG. 3 to optimize delivery of therapy (e.g., to optimize a pacing configuration).

Where information is received from the implanted device 100, a telemetry wand 1728 may be used. Other forms of wireless communication exist as well as forms of communication where the body is used as a "wire" to communicate information from the implantable device 100 to the programmer 1500.

If information is received directly from diagnostic equipment 1650, any appropriate input may be used, such as parallel IO circuit 1740 or serial IO circuit 1742. Motion information received via the device 100 or via other diagnostic equipment 1650 may be analyzed using the mapping system 1747. In particular, the mapping system 1747 (e.g., control logic) may identify positions within the body of a patient and associate such positions with one or more electrodes where such electrodes may be capable of delivering stimulation energy to the heart, performing other actions or be associated with one or more sensors.

A communication interface 1745 optionally allows for wired or wireless communication with diagnostic equipment 1650 or other equipment (e.g., equipment to ablate or otherwise treat a patient). The communication interface 1745 may be a network interface connected to a network (e.g., intranet, Internet, etc.).

A map or model of cardiac information may be displayed using display 1614 based, in part, on 3-D heart information and optionally 3-D torso information that facilitates interpretation of information. Such 3-D information may be input via ports 1740, 1742, 1745 from, for example, a database, a 3-D imaging system, a 3-D location digitizing apparatus (e.g., stereotactic localization system with sensors and/or probes) capable of digitizing the 3-D location. While 3-D information and localization are mentioned, information may be provided with fewer dimensions (e.g., 1-D or 2-D). For example, where motion in one dimension is insignificant to one or more other dimensions, then fewer dimensions may be used, which can simplify procedures and reduce computing requirements of a programmer, an implantable device, etc. The programmer 1500 optionally records procedures and allows for playback (e.g., for subsequent review). For example, a heart map and all of the electrical activation data, mechanical activation data, etc., may be recorded for subsequent review, perhaps if an electrode needs to be repositioned or one or more other factors need to be changed (e.g., to achieve an optimal configuration). Electrodes may be lead based or non-lead based, for example, an implantable device may operate as an electrode and be self powered and controlled or be in a slave-master relationship with another implantable device (e.g., consider a satellite pacemaker, etc.). An implantable device may use one or more epicardial electrodes.

Once all pacing leads are mounted and all pacing devices are implanted (e.g., master pacemaker, satellite pacemaker, biventricular pacemaker), the various devices are optionally further programmed.

The telemetry subsystem 1722 may include its own separate CPU 1724 for coordinating the operations of the telemetry subsystem. In a dual CPU system, the main CPU 1702 of programmer communicates with telemetry subsystem CPU 1724 via internal bus 1704. Telemetry subsystem additionally includes a telemetry circuit 1726 connected to telemetry wand 1728, which, in turn, receives and transmits signals electromagnetically from a telemetry unit of the implanted device. The telemetry wand is placed over the chest of the patient near the implanted device 100 to permit reliable transmission of data between the telemetry wand and the implanted device.

Typically, at the beginning of the programming session, the external programming device 1500 controls the implanted device(s) 100 via appropriate signals generated by the telemetry wand to output all previously recorded patient and device diagnostic information. Patient diagnostic information may include, for example, motion information (e.g., cardiac, respiratory, etc.) recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like.

Data retrieved from the implanted device(s) 100 can be stored by external programmer 1500 (e.g., within a random access memory (RAM) 1730, hard drive 1708, within a floppy diskette placed within floppy drive 1710). Additionally, or in the alternative, data may be permanently or semi-permanently stored within a compact disk (CD) or other digital media disk, if the overall system is configured with a drive for recording data onto digital media disks, such as a write once read many (WORM) drive. Where the programmer 1500 has a communication link to an external storage device or network storage device, then information may be stored in such a manner (e.g., on-site database, off-site database, etc.). The programmer 1500 optionally receives data from such storage devices.

A typical procedure may include transferring all patient and device diagnostic data stored in an implanted device 100 to the programmer 1500. The implanted device(s) 100 may be further controlled to transmit additional data in real time as it is detected by the implanted device(s) 100, such as additional motion information, IEGM data, lead impedance data, and the like. Additionally, or in the alternative, telemetry subsystem 1722 receives ECG signals from ECG leads 1732 via an ECG processing circuit 1734. As with data retrieved from the implanted device 100, signals received from the ECG leads are stored within one or more of the storage devices of the programmer 1500. Typically, ECG leads output analog electrical signals representative of the ECG. Accordingly, ECG circuit 1734 includes analog to digital conversion circuitry for converting the signals to digital data appropriate for further processing within programmer 1500. Depending upon the implementation, the ECG circuit 1743 may be configured to convert the analog signals into event record data for ease of processing along with the event record data retrieved from the implanted device. Typically, signals received from the ECG leads 1732 are received and processed in real time.

Thus, the programmer 1500 is configured to receive data from a variety of sources such as, but not limited to, the implanted device 100, the diagnostic equipment 1650 and directly or indirectly via external ECG leads (e.g., subsystem 1722 or external ECG system). The diagnostic equipment 1650 includes wired 1654 and/or wireless capabilities 1652 which optionally operate via a network that includes the programmer 1500 and the diagnostic equipment 1650 or data storage associated with the diagnostic equipment 1650.

Data retrieved from the implanted device(s) 100 typically includes parameters representative of the current programming state of the implanted devices. Under the control of the clinician, the external programmer displays the current programming parameters and permits the clinician to reprogram the parameters. To this end, the clinician enters appropriate commands via any of the aforementioned input devices and, under control of CPU 1702, the programming commands are converted to specific programming parameters for transmission to the implanted device 100 via telemetry wand 1728 to thereby reprogram the implanted device 100 or other devices, as appropriate.

Prior to reprogramming specific parameters, the clinician may control the external programmer 1500 to display any or all of the data retrieved from the implanted device 100, from the ECG leads 1732, including displays of ECGs, IEGMs, statistical patient information (e.g., via a database or other source), diagnostic equipment 1650, etc. Any or all of the information displayed by programmer may also be printed using a printer 1736.

A wide variety of parameters may be programmed by a clinician. In particular, for CRT, the AV delay and the VV delay of the implanted device(s) 100 are set to optimize cardiac function. In one example, the VV delay is first set to zero while the AV delay is adjusted to achieve the best possible cardiac function, optionally based on motion information. Then, VV delay may be adjusted to achieve still further enhancements in cardiac function.

Programmer 1500 optionally includes a modem to permit direct transmission of data to other programmers via the public switched telephone network (PSTN) or other interconnection line, such as a T1 line or fiber optic cable. Depending upon the implementation, the modem may be connected directly to internal bus 1704 may be connected to the internal bus via either a parallel port 1740 or a serial port 1742.

Other peripheral devices may be connected to the external programmer via the parallel port 1740, the serial port 1742, the communication interface 1745, etc. Although one of each is shown, a plurality of input output (IO) ports might be provided. A speaker 1744 is included for providing audible tones to the user, such as a warning beep in the event improper input is provided by the clinician. Telemetry subsystem 1722 additionally includes an analog output circuit 1746 for controlling the transmission of analog output signals, such as IEGM signals output to an ECG machine or chart recorder.

With the programmer 1500 configured as shown, a clinician or other user operating the external programmer is capable of retrieving, processing and displaying a wide range of information received from the ECG leads 1732, from the implanted device 100, the diagnostic equipment 1650, etc., and to reprogram the implanted device 100 or other implanted devices if needed. The descriptions provided herein with respect to FIG. 15 are intended merely to provide an overview of the operation of programmer and are not intended to describe in detail every feature of the hardware and software of the device and is not intended to provide an exhaustive list of the functions performed by the device 1500. Other devices, particularly computing devices, may be used.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
   positioning a lead in a patient wherein the lead comprises a longitudinal axis that extends from a proximal end to a distal end, wherein the lead comprises an electrode with an electrical center offset from the longitudinal axis of the lead body and wherein the lead comprises an anchoring screw at its distal end;
   rotating the anchoring screw;
   measuring electrical potential in a three-dimensional potential field using the electrode;
   determining the lead roll about the longitudinal axis of the lead body based on the measured electrical potential and the offset of the electrical center; and
   displaying a graphic indicating the determined lead roll.

2. The method of claim 1 further comprising displaying a graphic that indicates an axial position of the anchoring screw with respect to an axial position of the lead body.

3. The method of claim 1 wherein the rotating the anchoring screw comprises clockwise rotation, counter-clockwise rotation or clockwise and counter clockwise rotation.

* * * * *